(12) United States Patent
Gallégo

(10) Patent No.: US 12,256,198 B2
(45) Date of Patent: Mar. 18, 2025

(54) CONTROL OF PARAMETERS OF HEARING INSTRUMENT BASED ON EAR CANAL DEFORMATION AND CONCHA EMG SIGNALS

(71) Applicant: Starkey Laboratories, Inc., Eden Prairie, MN (US)

(72) Inventor: Stéphane Gallégo, Vénissieux (FR)

(73) Assignee: Starkey Laboratories, Inc., Eden Prairie, MN (US)

( * ) Notice: Subject to any disclaimer, the term of this patent is extended or adjusted under 35 U.S.C. 154(b) by 311 days.

(21) Appl. No.: 17/820,192

(22) Filed: Aug. 16, 2022

(65) Prior Publication Data

US 2022/0394396 A1    Dec. 8, 2022

Related U.S. Application Data

(63) Continuation of application No. PCT/US2021/018121, filed on Feb. 15, 2021.

(Continued)

(51) Int. Cl.
*H04R 25/00* (2006.01)
*A61B 5/00* (2006.01)
(Continued)

(52) U.S. Cl.
CPC .......... *H04R 25/505* (2013.01); *A61B 5/1114* (2013.01); *A61B 5/296* (2021.01);
(Continued)

(58) Field of Classification Search
CPC .................. H04R 25/505; H04R 25/40; H04R 2225/023; H04R 2225/41; H04R 2225/61;
(Continued)

(56) References Cited

U.S. PATENT DOCUMENTS 4,150,262 A    4/1979 Ono
5,161,533 A    11/1992 Prass et al.
(Continued)

FOREIGN PATENT DOCUMENTS

CN    105342613 A    2/2016
CN    205568942 U    9/2016
(Continued)

OTHER PUBLICATIONS

Ando et al., "CanalSense: Face-Related Movement Recognition System Based on Sensing Air Pressure in Ear Canals," Proceedings of the 30th Annual ACM Symposium on User Interface Software and Technology, Oct. 22-25, 2017, pp. 679-689.

(Continued)

*Primary Examiner* — Sunita Joshi
(74) *Attorney, Agent, or Firm* — Shumaker & Sieffert, P.A.

(57) ABSTRACT

A processing system obtains a deformation signal generated by a deformation sensor. The deformation signal is indicative of a deformation of an outer ear of a user of a hearing instrument. Additionally, the processing system obtains an EMG signal generated by an electrode in a concha of the user, wherein the electrode is configured to detect activity of an intrinsic auricular muscle of the user. Furthermore, the processing system generates information regarding an auditory attention state of the user based on the deformation signal and the EMG signal. The processing system controls, based on the information regarding the auditory attention state of the user, the parameter of the audio system.

20 Claims, 8 Drawing Sheets

Related U.S. Application Data

(60) Provisional application No. 62/979,249, filed on Feb. 20, 2020.

(51) Int. Cl.
  *A61B 5/11* (2006.01)
  *A61B 5/296* (2021.01)
  *A61B 5/297* (2021.01)
  *G01P 13/00* (2006.01)

(52) U.S. Cl.
  CPC ............ *A61B 5/297* (2021.01); *A61B 5/6815* (2013.01); *A61B 5/6843* (2013.01); *G01P 13/00* (2013.01); *H04R 25/40* (2013.01); *A61B 2562/0219* (2013.01); *H04R 2225/023* (2013.01); *H04R 2225/41* (2013.01); *H04R 2225/61* (2013.01)

(58) Field of Classification Search
  CPC ....... A61B 5/296; A61B 5/297; A61B 5/1114; A61B 5/6815
  See application file for complete search history.

(56) References Cited

U.S. PATENT DOCUMENTS

| | | |
|---|---|---|
| 5,737,431 A | 4/1998 | Brandstein et al. |
| 5,800,351 A | 9/1998 | Mann et al. |
| 6,032,065 A | 2/2000 | Brown |
| 6,422,999 B1 | 7/2002 | Hill |
| 6,453,194 B1 | 9/2002 | Hill |
| 6,625,481 B2 | 9/2003 | Bennett et al. |
| 6,636,763 B1 | 10/2003 | Junker et al. |
| 7,148,878 B2 | 12/2006 | Hong et al. |
| 7,529,379 B2 | 5/2009 | Zurek et al. |
| 7,554,549 B2 | 6/2009 | Sagar et al. |
| 7,593,769 B1 | 9/2009 | Ettare |
| 7,627,470 B2 | 12/2009 | Manabe et al. |
| 7,914,468 B2 | 3/2011 | Shalon et al. |
| 8,467,562 B2 | 6/2013 | Wada |
| 8,504,146 B2 | 8/2013 | Joshi et al. |
| 8,565,852 B2 | 10/2013 | Wada et al. |
| 8,639,320 B2 | 1/2014 | Tomita et al. |
| 8,768,477 B2 | 7/2014 | Spitzer et al. |
| 8,894,718 B2 | 11/2014 | Sala et al. |
| 8,989,857 B2 | 3/2015 | Heck |
| 9,042,586 B2 | 5/2015 | Burns et al. |
| 9,210,517 B2 | 12/2015 | Pontoppidan et al. |
| 9,294,849 B2 | 3/2016 | Burns et al. |
| 9,344,792 B2 | 5/2016 | Rundle |
| 9,372,533 B1 | 6/2016 | Agrama |
| 9,846,483 B2 | 12/2017 | Petrov |
| 10,063,960 B2 | 8/2018 | Aase |
| 10,121,063 B2 | 11/2018 | Von und zu Liechtenstein |
| 10,137,363 B2 | 11/2018 | Parshionikar |
| 10,191,558 B2 | 1/2019 | Parshionikar |
| 10,609,494 B2 | 3/2020 | Hannemann et al. |
| 10,924,869 B2 | 2/2021 | Gallégo |
| 11,350,831 B2 | 6/2022 | Leboeuf et al. |
| 2006/0058627 A1 | 3/2006 | Flaherty et al. |
| 2006/0061544 A1 | 3/2006 | Min et al. |
| 2008/0218472 A1 | 9/2008 | Breen et al. |
| 2009/0005700 A1 | 1/2009 | Joshi et al. |
| 2009/0062680 A1 | 3/2009 | Sandford |
| 2011/0125063 A1 | 5/2011 | Shalon et al. |
| 2011/0276312 A1 | 11/2011 | Shalon et al. |
| 2012/0116537 A1 | 5/2012 | Liebetanz |
| 2012/0149467 A1 | 6/2012 | Heck |
| 2012/0245655 A1 | 9/2012 | Spitzer et al. |
| 2013/0123656 A1 | 5/2013 | Heck |
| 2014/0288447 A1 | 9/2014 | Luna et al. |
| 2015/0063615 A1 | 3/2015 | Park et al. |
| 2015/0157255 A1 | 6/2015 | Nduka |
| 2016/0119726 A1 | 4/2016 | Pontoppidan et al. |
| 2016/0143079 A1 | 5/2016 | Keun et al. |
| 2016/0243362 A1 | 8/2016 | Herhmann et al. |
| 2016/0262689 A1 | 9/2016 | Batista |
| 2017/0060256 A1 | 3/2017 | Heck et al. |
| 2017/0180882 A1 | 6/2017 | Lunner et al. |
| 2017/0318398 A1 | 11/2017 | Merks |
| 2018/0074584 A1 | 3/2018 | Rüdiger et al. |
| 2018/0107275 A1 | 4/2018 | Chen et al. |
| 2018/0193644 A1 | 7/2018 | Annoni et al. |
| 2018/0263562 A1 | 9/2018 | LaPlante-Levesque et al. |
| 2018/0321173 A1 | 11/2018 | Hanein et al. |
| 2018/0368722 A1* | 12/2018 | Lunner .................. G06F 3/013 |
| 2019/0008435 A1 | 1/2019 | Cakmak |
| 2019/0025919 A1 | 1/2019 | Tadi et al. |
| 2019/0052977 A1 | 2/2019 | Hannemann et al. |
| 2019/0052978 A1* | 2/2019 | Hannemann ......... H04R 25/552 |
| 2019/0265802 A1 | 8/2019 | Parshionikar |
| 2022/0394396 A1 | 12/2022 | Gallégo |

FOREIGN PATENT DOCUMENTS

| | | |
|---|---|---|
| CN | 106175758 A | 12/2016 |
| CN | 106569607 A | 4/2017 |
| CN | 206470693 U | 9/2017 |
| CN | 108542387 A | 9/2018 |
| CN | 108670241 A | 10/2018 |
| CN | 109391891 A | 2/2019 |
| DE | 102015206450 A1 | 10/2016 |
| DE | 102017214164 B3 | 1/2019 |
| EP | 1519625 A2 | 3/2005 |
| EP | 1854404 B1 | 11/2007 |
| EP | 2442758 B1 | 5/2013 |
| EP | 2830493 A1 | 2/2015 |
| EP | 3105600 A1 | 12/2016 |
| EP | 3445067 A1 | 2/2019 |
| EP | 3445068 B1 | 1/2020 |
| GB | 2396421 A | 6/2004 |
| JP | 2019036959 A | 3/2019 |
| KR | 100516151 A | 2/2003 |
| KR | 101788709 B1 | 3/2016 |
| KR | 101785500 B1 | 8/2017 |
| KR | 20180056231 A | 5/2018 |
| KR | 101910021 B1 | 10/2018 |
| RU | 2312588 C1 | 12/2007 |
| WO | 2006033104 A1 | 3/2006 |
| WO | 2012129465 A1 | 9/2012 |
| WO | 2013144229 A1 | 10/2013 |
| WO | 2014055382 A1 | 4/2014 |
| WO | 2014152055 A2 | 9/2014 |
| WO | 2014176420 A1 | 10/2014 |
| WO | 2015017790 A | 2/2015 |
| WO | 2015123425 A1 | 8/2015 |
| WO | 2018027141 A1 | 2/2018 |
| WO | 2018103861 A1 | 6/2018 |
| WO | 2018218086 A1 | 11/2018 |
| WO | 2019051613 A1 | 3/2019 |

OTHER PUBLICATIONS

Bedri et al., "Stick It In Your Ear: Building an In-Ear Jaw Movement Sensor," UbiComp/ISWC Adjunct, Sep. 7-11, 2015, pp. 1333-1338.

Benning et al., "Emotional modulation of the post-auricular reflex", Psychophysiology, vol. 41, No. 3, May 2004, pp. 426-432.

Benning, "Postauricular and superior auricular reflex modulation during emotional pictures and sounds", Psychophysiology, vol. 48, No. 3, Mar. 2011, p. 410-414.

Benning, "The Postauricular Reflex as a Measure of Attention and Positive Emotion.", Oxford Academic, Apr. 5, 2018, 17 pp.

Carioli et al., "Piezoelectric Earcanal Bending Sensor," IEEE Sensors Journal, vol. 18, No. 5, Mar. 1, 2018, pp. 2060-2067.

Chi et al., "Dry-Contact and Noncontact Biopotential Electrodes: Methodological Review", IEEE Reviews in Biomedical Engineering, vol. 3, Oct. 11, 2010, pp. 106-119.

Cody et al., "Averaged Evoked Myogenic Responses in Normal Man," The Laryngoscope, vol. 79, No. 3, Apr. 1969, pp. 400-416.

Colin, "Influence de la Surdite Neurosensorielle sur la Perception de la Hauteur Tonale," Neurosciences, University of Lyon, In the French Language with English Abstract, Dec. 12, 2016, 200 pp.

(56) References Cited

OTHER PUBLICATIONS

De Grandis et al., "The Post-Auricular Response. A Single Motor Unit Study," Electroencephalography and Clinical Neurophysiology, vol. 50, May 21, 1980, pp. 437-440.
Douek et al., "A Single Average Crossed Acoustic Response," The Journal of Layngology and Otology, vol. 90, No. 11, Dec. 1976, pp. 1027-1032.
Douek et al., "The Crossed Acoustic Response and Objective Tests of Hearing," Development Medicine and Child Neurology, vol. 16, No. 1, Feb. 1974, pp. 32-39.
Douek et al., "The Crossed Acoustic Response," The Journal of Layngology and Otology, vol. 87, No. 8, Aug. 1973, pp. 711-726.
Dus et al., "The Click Evoked Post-Auricular Myogenic Response in Normal Subjects," Electroencephalography and Clinical Neurophysiology, vol. 39, Jun. 13, 1975, pp. 523-525.
Grenness et al., "Mapping ear canal movement using area-based surface matching", The Journal of the Acoustical Society of America, vol. 111, No. 2, Feb. 11, 2002, pp. 960-971.
Guevara, "Amelioration de L'implant Cochleaire Oticon Neurelec et de son Pronostic : de L'ingenierie a la Stimulation Neurale," Neurosciences, University of Lyon, English Abstract Only, Dec. 18, 2015, 2 pp.
Hackley et al., "Combined Use of Microflexes and Event-Related Brain Potentials as Measures of Auditory Selective Attention," Psychophysiology, vol. 24, No. 6, Nov. 1987, pp. 632-647.
Hackley et al., "Evidence for a Vestigial Pinna-Orienting System in Humans," Psychophysiology, vol. 52, No. 10, Jul. 2015, pp. 1263-1270.
Huigen et al., "Investigation into the origin of the noise of surface electrodes", Medical and Biological Engineering and Computing, vol. 40, Jun. 2002, p. 332-338.
International Preliminary Report on Patentability from International Application No. PCT/US2021/018121 dated Sep. 1, 2022, 8 pp.
International Search Report and Written Opinion of International Application No. PCT/US2021/018121 dated May 14, 2021, 13 pp.
Jacobson et al., "The Vestibular Evoked Myogenic Potential and Other Sonomotor Evoked Potentials," In: Auditory evoked potentials: basic principles and clinical application, Chapter 27, 2007, (Applicant points out, in accordance with MPEP 609.04(a), that the year of publication, 2007, is sufficiently earlier than the effective U.S. filing date, so that the particular month of publication is not in issue.), pp. 572-593.
Johnson et al., "The nursing hypothesis: an evolutionary account of emotional modulation of the postauricular reflex", Psychophysiology, vol. 49, No. 2, Feb. 2012, pp. 178-185.
Kaneko et al., "Detecting the Direction of Listening with the Emg Signals Measured Behind Ears," In Proceedings of the SIGCHI Conference on Human Factors in Computing Systems, Apr. 5-10, 2008 , pp. 535-538.
Kappel et al., "Physiological artifacts in scalp EEG and ear-EEG", BioMedical Engineering OnLine volume, Aug. 11, 2017, 16 pp.
Keidser et al., "The Effect of Multi-Channel Wide Dynamic Range Compression, Noise Reduction, and the Directional Microphone on Horizontal Localization, Performance in Hearing Aid Wearers," International Journal of Audiology, vol. 45, No. 10, Feb. 7, 2006, pp. 563-579.
Kiang et al., "Post-Auricular Electric Response to Acoustic Stimuli in Humans," Quarterly Progress Report, Lab of Electronics, M.I.T., No. 68, Jan. 15, 1963, pp. 218-226.
Maag et al., "BARTON: Low Power Tongue Movement Sensing with In-ear Barometers," 2017 IEEE 23rd International Conference on Parallel and Distributed Systems, Dec. 15-17, 2017, pp. 9-16.

Mirkovic et al., "Target Speaker Detection with Concealed EEG Around the Ear," Frontiers in Neuroscience, vol. 10, Article 349, Jul. 2016, 11 pp.
Moonen et al., "Horizontal Localization With Bilateral Hearing Aids: Without is Better Than With," The Journal of the Acoustical Society of America, vol. 119, No. 1, Jan. 2006, pp. 515-526.
O'Beirne et al., "Basic Properties of the Sound-Evoked Post-Auricular Muscle Response (PAMR)," Hearing Research, vol. 138, Aug. 23, 1999, pp. 115-132.
O'Beirne et al., "The Post-Auricular Muscle Reflex (PAMR): Its Detection, Analysis, and Use as an Objective Hearing Test," retrieved from http://ir.canterbury.ac.nz/handle/10092/11083, Nov. 1998, 261 pp.
Oliveira et al., "A look at ear canal changes with jaw motion", Ear Hear, Dec. 1993, pp. 464-466.
Patuzzi et al., "Effects of Eye Rotation on the Sound-Evoked Post-Auricular Muscle Response (PAMR)," Hearing Research, vol. 138, Dec. 1999, pp. 133-146.
Picton et al., "Human Auditory Evoked Potentials. I : Evaluation of Components," Electroencephalography and Clinical Neurophysiology, vol. 36, Aug. 1973, pp. 179-190.
Prosecution History from U.S. Appl. No. 16/271,281, now issued U.S. Pat. No. 10,924,869, dated May 14, 2020, through Dec. 18, 2020, 46 pp.
Purdy et al., "The Post-Auricular Muscle Response: An Objective Electrophysiological Method for Evaluating Hearing Sensitivity," International Journal of Audiology, vol. 44, No. 11, Dec. 2005, pp. 625-630.
Rabinkin et al., "Optimum Microphone Placement for Array Sound Capture," The Journal of the Acoustical Society of America, Jul. 1997, 13 pp.
Schmalfu et al., "Steer by Ear: Myoelectric Auricular Control of Powered Wheelchairs for Individuals with Spinal Cord Injury," Restorative Neurology and Neuroscience, vol. 34, No. 1, Jan. 2015, pp. 79-95.
Schmidt et al., "Co-Activation of the M. transversus auris with Eye Movements (Wilson's Oculo-Auricular Phenomenon) and with Activity in Other Cranial Nerves," Albrecht Von Graefe's Archive for Clinical and Experimental Ophthalmology, vol. 206, No. 4, Jul. 1978, pp. 227-236.
Stekelenburg et al., "Pericranial Muscular, Respiratory, and Heart Rate Components of the Orienting Response," Psychophysiology, vol. 39, Dec. 2002, pp. 707-722.
Streletz et al. "Scalp Recorded Auditory Evoked Potentials and Sonomotor Responses: an Evaluation of Components and Recording Techniques," Electroencephalography and Clinical Neurophysiology, vol. 43, No. 2, Sep. 1977, pp. 192-206.
Thornton et al., "The Use of Post-Auricular Muscle Responses," The Journal of Laryngology & Otology, vol. 89, No. 10, Oct. 1975, pp. 997-1010.
Urban et al., "The oculo-auricular phenomenon: Findings in normal and patients with brainstem lesions", Brain, vol. 116, No. 3, Jun. 1, 1993, pp. 727-738.
Valin et al., "Robust Sound Source Localization Using a Microphone Array on a Mobile Robot," Proceedings IEEE/RSJ International Conference on Intelligent Robots and Systems (IROS) 2003, Apr. 2004, pp. 1228-1233.
Wong et al., "Decoding Speech Sound Source Direction from Electroencephalography Data," ARO Abstracts vol. 39, ARO 39th Mid Winter Meeting, Feb. 21, 2016, p. 528.
Yoshie et al., "Myogenic Evoked Potential Responses to Clicks in Man," Acta Oto-Laryngolica Supplementum, vol. 252, Feb. 1969, pp. 89-103.

* cited by examiner

CONTROL OF PARAMETERS OF HEARING INSTRUMENT BASED ON EAR CANAL DEFORMATION AND CONCHA EMG SIGNALS

This application is a continuation of International Application No. PCT/US2021/018121, filed on Feb. 15, 2021, which claims priority to U.S. Provisional Patent Application 62/979,249, filed Feb. 20, 2020, the entire content of both of which are incorporated by reference herein.

TECHNICAL FIELD

This disclosure relates to hearing instruments.

BACKGROUND

Hearing instruments are devices designed to be worn on, in, or near one or more of a user's ears. Common types of hearing instruments include hearing assistance devices (e.g., "hearing aids"), earbuds, headphones, hearables, cochlear implants, and so on. In some examples, a hearing instrument may be implanted or integrated into a user. Some hearing instruments include additional features beyond just environmental sound-amplification. For example, some modern hearing instruments include advanced audio processing for improved device functionality, controlling and programming the devices, and beamforming, and some can communicate wirelessly with external devices including other hearing instruments (e.g., for streaming media).

SUMMARY

This disclosure describes techniques for generating information regarding a user's auditory reactions to sound, auditory attentional state, or listening intent, or for improving such detection or classification, based on a combination of deformation signals measured by at least one deformation sensor in an ear canal of the user and electromyographic (EMG) signals measured using at least one electrode in a concha of the user, or from a combination of both of these two types of signals with other signals measured by other sensors. Furthermore, the disclosure describes techniques for setting or changing operational characteristics of an audio system based on the results of the detection or classification.

In one example, this disclosure describes a method for controlling a parameter of an audio system, the method comprising: obtaining, by a processing system, a deformation signal generated by a deformation sensor, wherein the deformation signal is indicative of a deformation of an ear of a user of a hearing instrument; obtaining, by the processing system, an electromyographic (EMG) signal generated by an electrode in a concha of the user, wherein the EMG signal is indicative of activity of an intrinsic auricular muscle of the user; generating, by the processing system, information regarding an auditory attention state of the user based on the deformation signal and the EMG signal; and controlling, by the processing system, based on the information regarding the auditory attention state of the user, the parameter of the audio system.

In another example, this disclosure describes an audio system comprising: a deformation sensor configured to generate a deformation signal indicative of a deformation of an ear of a user of a hearing instrument; an electrode configured to generate an electromyographic (EMG) signal indicative of activity of an intrinsic auricular muscle of the user of the hearing instrument; a processing system comprising one or more processing circuits, the processing system configured to: obtain the deformation signal generated by the deformation sensor; obtain the EMG signal generated by the electrode; generate information regarding an auditory attention state of the user based on the deformation signal and the EMG signal; and control, based on the information regarding the auditory attention state of the user, the parameter of the audio system.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
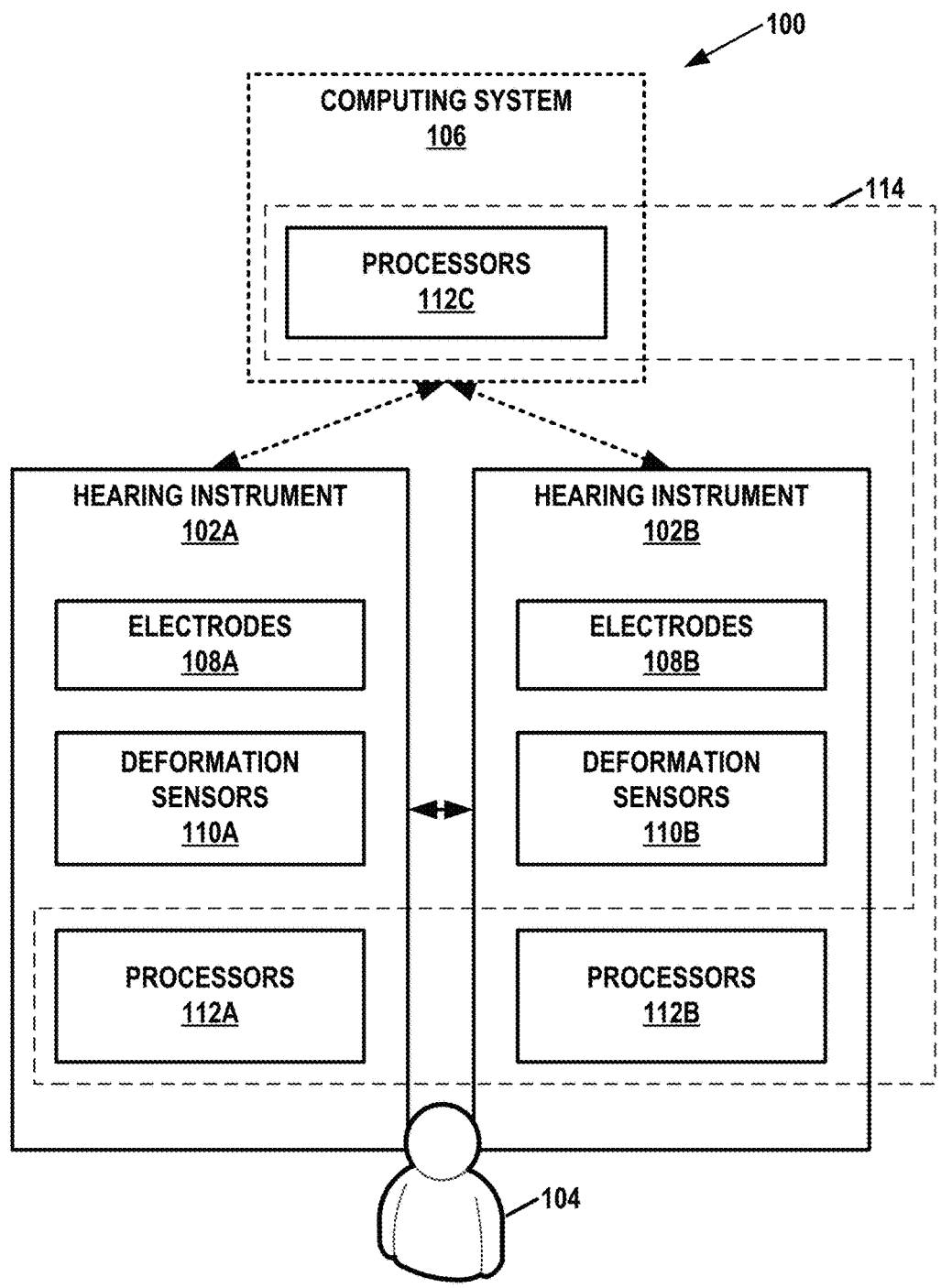
FIG. 1 is a conceptual diagram illustrating an example audio system that includes hearing instruments, in accordance with one or more examples of this disclosure.

Audio systems are widespread today and come in various forms, including but not limited to, head- or ear-worn devices such as headphones or earphones. Audio systems can fulfill various functions, including but not limited to, sound reproduction, sound enhancement, or other types of sound processing for communication (e.g., cellphones, teleconference systems, hearables), personal entertainment (e.g., music, movies, games), assisted listening (e.g., hearing aids), or other purposes. In the context of this disclosure, such systems may be generally referred to as "audio systems."

A limitation for most current audio systems today stems from their lack or scarcity of inputs providing information regarding the current cognitive or perceptual state of their users, including the current auditory attentional state or listening intentions of their users. Listening intentions may include, for example, wanting to listen to certain sounds. Most audio systems today lack inputs for indicating the sounds to which a user of the system wants to listen. For example, a user might want to listen to a particular voice in an audio recording at one time, but to another voice a few seconds later. An individual's auditory attention state includes, for example, whether the individual is currently attending to sound or not, and if so, sounds on which the individual's attention is focused.

Endowing an audio system with such inputs, and a way to process these inputs, may enable various improvements in the system's function and, ultimately, in enhanced user experience. For instance, being able to automatically track over time which sound a user is attending to, or intending to listen to, could allow, facilitate, or enhance the automatic activation of specific sound enhancement algorithms, such as noise suppression algorithms or directional sound processing algorithms, e.g., algorithms that selectively amplify, or selectively attenuate, sounds coming from certain directions relative to the user. The use of such systems may be particularly advantageous for hearing impaired listeners, or in "noisy" or multi-source acoustic environments, in which even individuals with normal hearing can experience listening difficulties. For instance, it could allow the automatic selective amplification of sounds (e.g., the voice of an interlocutor of the user in a crowded restaurant) that the user wants to listen to, while attenuating sounds which the user is trying to ignore, such as voices coming from other directions or background noises.

Previous attempts to design such a system have involved, for example, a smartphone application or gesture interface, which can be on the audio device, and whereby a user can provide information regarding his/her listening intentions. For example, whether the user wishes to turn the volume up or down, or to primarily hear sounds coming from in front of the user. The interface then issues a command signal to an audio device, e.g., a hearing instrument. However, this type of solution, which involves manual or other gesture input from the user, is demanding (e.g., the user must provide input whenever his/her listening state or intentions change), intrusive (e.g., the user must temporarily disengage from what they are doing to provide such input) and not discreet (e.g., the user must make gestures in order to interact manually with the input device, including gestures that may be visible to others).

Other attempts to solve this problem have used biometric measures, such as electrooculography (EOG), electroencephalography (EEG), or electromyography (EMG), to try to generate information regarding the user's cognitive or auditory state, such as whether the user currently wants to listen to sounds arriving from a particular direction, based on eye movements (EOG), brain activity (EEG), or auricular muscles (EMG). Hearing instruments or other audio devices may comprise an element located inside, or proximate to, their users' ears that generate biometric electrical signals. For instance, electrodes placed in, on, or around the users' ears can generate the biometric electrical signals.

However, in actual practice, these previous attempts may suffer from one or several practical shortcomings for everyday use in consumer electronics or hearing instrument devices. For example, while EOG, EEG and EMG are customarily and most reliably obtained using wet electrodes, which comprise a gel layer on their surface, such wet electrodes are of limited practical use, especially for commercial applications, due to various constraints associated with their use. These constraints may include: the requirement for skin preparation, which usually involves abrasion of the superficial skin layer; degradation in signal fidelity as the gel dries; unpleasant sensations for the user during and after the application of gel; and the potential for allergic reactions and irritation. For this reason, non-gel electrodes may appear to be a more practical option for commercial applications in products that users can wear often, and for protracted periods of time.

Unfortunately, attempts to measure EMG, EEG, or EOG signals using dry (non-gel) electrodes on the surface of an ear-worn device are of limited use as everyday solutions due to the electrode-skin interface being adversely impacted by (1) motion artifacts, e.g., momentary variations in the impedance due to movements of biological tissues with which the electrode is in contact and (2) ear secretions. Ear secretions, including cerumen and perspiration, are most likely to impact the quality of electrical signals recorded using one or more electrode inside the ear canal, such as electrodes placed on the surface of an in-the-canal (ITC) device. This problem is likely to be worse for devices that close the ear canal of the user, as this increases the likelihood that secretions are produced and trapped inside the ear canal. Motion artifacts caused by head or neck movements during, for example, walking, running, or simply, head turns while sitting or standing, are especially likely to limit practical applications that seek to use electrodes located on the surface of a behind-the-ear (BTE) device, which is currently the most commercially widespread hearing aid form factor throughout the world, and is also used for certain earphones, especially, for sports. Jaw movements, such as during opening and closing of the mouth, or chewing, can limit applications that seek to use electrodes in the ear canal. Indeed, ear canal geometry is substantially modified by opening and closing of the mouth, and can also be modified by facial gestures such as smiling, yawning, or talking, and such displacements of ear canal tissues, or the associated EEG or EMG signals, can generate artifacts and strongly interfere with, or prevent, the measurement of the target EEG or EMG signals.

Motion artifacts caused by head, neck, or jaw movement also pose a problem for practical applications of attempts to measure periauricular muscle contractions using mechanical sensors, such as pressure sensors. Jaw movements, in particular, can produce deformations of ear canal tissues, which can severely impact the measurement of periauricular muscle activity using one or more displacement sensors inside the ear canal of a user, for example, while the user is talking or chewing, or making certain facial gestures, such as smiling. A second problem with attempts to use mechanical displacement sensors for measuring the activity (e.g., motor and/or electrical activity) of auricular muscles in commercial products stems from the fact that such activity does not always produce detectable displacements or deformations of surrounding ear canal tissues. This is because, firstly, auricular muscles are small and weak, and these muscles may fail to induce contractions that are sufficiently large to induce movements of ear tissues that are reliably detectable with mechanical displacement sensors, even when these same muscles produce detectable EMG signals.

Moreover, involuntary periauricular muscle activities associated with the activation of other facial muscles can also induce motion artifacts in signals measured using electrodes or deformation sensors inside the ear, especially, when these sensors are placed inside the ear canal or behind the pinna, two locations that are most strongly influenced by extrinsic auricular muscle activity.

The limitations outlined above are compounded in previous attempts to use electrical or mechanical measures of auricular muscle signals to detect or classify auditory reactions or listening intentions of a user have focused either exclusively, or preferentially, on the extrinsic auricular muscle (i.e., periauricular muscles). The extrinsic auricular muscles are the posterior auricular muscle, the anterior auricular muscle, and the superior auricular muscle. The posterior auricular muscle has been most thoroughly studied. Under controlled laboratory conditions, it has been shown that EMG signals from the posterior auricular muscle may provide information on a user's reactions to sound. The anatomical location of the posterior auricular muscle is potentially advantageous for applications involving a behind-the-ear (BTE) or in-the-ear canal (ITC) device, making the posterior auricular muscle a target of choice in attempts to develop such applications. However, in addition to the obstacles listed above, such as motion artifacts during jaw or head movements, such attempts are likely to be limited in practice by at least two problems. Firstly, the posterior auricular muscle responses to sound have been found to be highly variable among individuals. In some individuals, such responses cannot be reliably detected, even using gel electrodes placed on the surface of the posterior auricular muscle, unless the individual's eyes are fully rotated toward the same side as the one on which the EMG recording is being made. This is likely to limit attempts to develop practical applications using EMG signals from the posterior auricular muscle to reliably detect or classify auditory reactions or listening intentions of a user outside situations in which eye movements can be tightly controlled.

A second problem for attempts to use extrinsic auricular muscle signals, and in particular, posterior auricular muscle signals in commercial applications to detect or classify auditory reactions or listening intentions of a user, is that the responses of these muscles can be modulated (e.g., potentiated or inhibited) by the user's emotional state. For example, responses of the posterior auricular muscle to sounds can be modulated (e.g., enhanced) depending on the emotional state of the individual, which may be influenced while viewing pictures. This creates a problem for practical applications of attempts to use solely electrical or mechanical signals from the extrinsic auricular muscles to determine, specifically, auditory reactions, auditory attentional state, or listening intentions of a user, because in this context, emotional modulation of extrinsic auricular muscle responses unrelated to the user's auditory reactions, auditory attentional state or listening intentions, introduce an unwanted source of variability in the determination of such reactions, states, or intentions.

Another potential problem for attempts to use extrinsic auricular muscle signals, and in particular, posterior auricular muscle signals in commercial applications to detect or classify auditory reactions or listening intentions of a user, is that extrinsic auricular muscles can be strongly activated during certain facial gestures, such as smiling or raising of the eyebrows (e.g., during the facial expression of surprise).

This disclosure describes techniques for detecting or classifying reactions to sound, attentional state, or listening intentions of a user, or for improving such detection or classification by combining physical deformation signals measured using a deformation sensor in an ear canal of the user with EMG signals (e.g., EMG signals) measured using at least one electrode in a concha of the same user, or by further combining said ear canal deformation and concha EMG signals with other signals, including but not limited to EOG, EEG, acoustic, head position or head motion signals, measured using electrodes, optical sensors, microphones, displacement sensors or motion sensors.

As described in this disclosure, a processing system controls a parameter of an audio system. For example, the processing system may obtain a deformation signal generated by a deformation sensor. The deformation signal is indicative of a deformation of an ear of a user of a hearing instrument. Additionally, the processing system obtains an EMG signal generated by an electrode in a concha of the user. The electrode is configured to detect activity (e.g., motor and/or electrical activity) of an intrinsic auricular muscle of the user, such as a transverse auricular muscle. The processing system may generate information regarding an auditory attention state of the user based on the deformation signal and the EMG signal. The processing system may control, based on the auditory attention state of the user, a parameter of the audio system. As described herein, the use of the EMG generated by an electrode configured to detect activity of an intrinsic auricular muscle, in combination with the deformation signal, to generate information regarding the auditory attention state of the user may address one or more of the problems described above.

FIG. 1 is a conceptual diagram illustrating an example audio system 100 that includes hearing instruments 102A, 102B, in accordance with one or more examples of this disclosure. This disclosure may refer to hearing instruments 102A and 102B collectively, as "hearing instruments 102." A user 104 may wear hearing instruments 102. In some instances, such as when user 104 has unilateral hearing loss, user 104 may wear a single hearing instrument. In other instances, such as when user 104 has bilateral hearing loss, user 104 may wear two hearing instruments, with one hearing instrument 102A, 102B, respectively, for each ear of user 104.

Hearing instruments 102 may comprise one or more of various types of devices that are configured to provide auditory stimuli to a user and that are designed for wear and/or implantation at, on, or near an ear of user 104. Hearing instruments 102 may be worn, at least partially, in the ear canal or concha. One or more of hearing instruments 102 may include behind the ear (BTE) components that are worn behind the ears of user 104. In some examples, hearing instruments 102 comprise devices that are at least partially implanted into or integrated with the skull of user 104. In some examples, one or more of hearing instruments 102 is able to provide auditory stimuli to user 104 via a bone conduction pathway.

In any of the examples of this disclosure, each of hearing instruments 102 may comprise a hearing assistance device. Hearing assistance devices include devices that help a user hear sounds in the user's environment. Example types of hearing assistance devices may include hearing aid devices, Personal Sound Amplification Products (PSAPs), cochlear implant systems (which may include cochlear implant magnets, cochlear implant transducers, and cochlear implant processors), and so on. In some examples, hearing instruments 102 are over-the-counter, direct-to-consumer, or prescription devices. Furthermore, in some examples, hearing instruments 102 include devices that provide auditory stimuli to user 104 that correspond to artificial sounds or sounds that are not naturally in the user's environment, such as recorded music, computer-generated sounds, or other types of sounds. For instance, hearing instruments 102 may include so-called "hearables," earbuds, earphones, or other types of devices. Some types of hearing instruments provide auditory stimuli to user 104 corresponding to sounds from the user's environmental and also artificial sounds.

In some examples, one or more of hearing instruments 102 includes a housing or shell that is designed to be worn in the ear for both aesthetic and functional reasons and encloses the electronic components of the hearing instrument. Such hearing instruments may be referred to as in-the-ear (ITE), in-the-canal (ITC), completely-in-the-canal (CIC), or invisible-in-the-canal (IIC) devices. In some examples, one or more of hearing instruments 102 may be behind-the-ear (BTE) devices, which include a housing worn behind the ear that contains all of the electronic components of the hearing instrument, including the receiver (e.g., a speaker). The receiver conducts sound to an earbud inside the ear via an audio tube. In some examples, one or more of hearing instruments 102 may be receiver-in-canal (RIC) hearing-assistance devices, which include a housing worn behind the ear that contains electronic components and a housing worn in the ear canal that contains the receiver.

Hearing instruments 102 may implement a variety of features that help user 104 hear better. For example, hearing instruments 102 may amplify the intensity of incoming sound, amplify the intensity of certain frequencies of the incoming sound, translate or compress frequencies of the incoming sound, and/or perform other functions to improve the hearing of user 104. In another example, hearing instruments 102 may implement a directional processing mode in which hearing instruments 102 selectively amplify sound originating from a particular direction (e.g., to the front of user 104) while partially canceling sound originating from other directions. In other words, a directional processing mode may selectively attenuate off-axis unwanted sounds. The directional processing mode may help users understand conversations occurring in crowds or other noisy environments. In some examples, hearing instruments 102 may use beamforming or directional processing cues to implement or augment directional processing modes.

In some examples, hearing instruments 102 may reduce noise by canceling out or attenuating certain frequencies. Furthermore, in some examples, hearing instruments 102 may help user 104 enjoy audio media, such as music or sound components of visual media, by outputting sound based on audio data wirelessly transmitted to hearing instruments 102.

Hearing instruments 102 may be configured to communicate with each other. For instance, in any of the examples of this disclosure, hearing instruments 102 may communicate with each other using one or more wireless communication technologies. Example types of wireless communication technology include Near-Field Magnetic Induction (NFMI) technology, a 900 MHz technology, a BLUETOOTH™ technology, a WI-FI™ technology, audible sound signals, ultrasonic communication technology, infrared communication technology, an inductive communication technology, or another type of communication technology that does not rely on wires to transmit signals between devices. In some examples, hearing instruments 102 use a 2.4 GHz frequency band for wireless communication. In examples of this disclosure, hearing instruments 102 may communicate with each other via non-wireless communication links, such as via one or more cables, direct electrical contacts, and so on.

As shown in the example of FIG. 1, audio system 100 may also include a computing system 106. In other examples, audio system 100 does not include computing system 106. Computing system 106 comprises one or more computing devices, each of which may include one or more processors 112C. For instance, computing system 106 may comprise one or more mobile devices, server devices, personal computer devices, handheld devices, wireless access points, smart speaker devices, smart televisions, medical alarm devices, smart key fobs, smartwatches, smartphones, motion or presence sensor devices, smart displays, screen-enhanced smart speakers, wireless routers, wireless communication hubs, prosthetic devices, mobility devices, special-purpose devices, accessory devices, and/or other types of devices. Accessory devices may include devices that are configured specifically for use with hearing instruments 102. Example types of accessory devices may include charging cases for hearing instruments 102, storage cases for hearing instruments 102, media streamer devices, phone streamer devices, external microphone devices, remote controls for hearing instruments 102, and other types of devices specifically designed for use with hearing instruments 102. Actions described in this disclosure as being performed by computing system 106 may be performed by one or more of the computing devices of computing system 106. One or more of hearing instruments 102 may communicate with computing system 106 using wireless or non-wireless communication links. For instance, hearing instruments 102 may communicate with computing system 106 using any of the example types of communication technologies described elsewhere in this disclosure.

In the example of FIG. 1, hearing instrument 102A includes a set of one or more electrodes 108A and a set of one or more deformation sensors 110A. Similarly, in the example of FIG. 1, hearing instrument 102B includes a set of one or more electrodes 108B and a set of one or more deformation sensors 110B. Collectively, this disclosure may refer to electrodes 108A and electrodes 108B as "electrodes 108." Similarly, this disclosure may refer collectively to deformation sensors 110A and deformation sensors 110B as "deformation sensors 110."

Electrodes 108A are configured to measure electromyographic (EMG) signals indicative of auricular muscles of user 104. Example auricular muscles of user 104 may include periauricular muscles and intrinsic auricular muscles. The periauricular muscles are located around the peripheries of the ears of user 104. The intrinsic auricular muscles are located within the ears of user 104.

Deformation sensors 110 are configured to generate deformation signals indicative of deformation of the ears of user 104. In the context of this disclosure, a deformation of an ear refers to a change in the geometry of any portion of the ear, such as displacements of ear tissues (skin, cartilage, bone, etc.). Such deformations may occur in the ear canal, pinna, or other parts of the user's ear. Deformations of the user's ear can result from displacements of the head or other body parts, or from activities of muscles, especially, of the head or neck, including but not limited to, facial muscles, auricular muscles (e.g., intrinsic auricular muscles or periauricular muscles), jaw muscles, the jaw bone, and the tongue. As described in this disclosure, deformations of the user's ears, in combination with the EMG signals generated by electrodes 108, may be used for the purpose of generating information regarding the user's auditory attention state.

In accordance with some techniques of this disclosure, deformation sensors 110 may be implemented using electrical (e.g., inductive, capacitive, resistive), electro-mechanical (e.g., piezo-electric), optical (e.g., infrared proximity sensor), or other types of sensors (e.g., pressure sensors, such as barometers). In some examples of this disclosure, deformation sensors 110 may be mounted on custom-fitted earpieces (e.g., custom mold or standard mold subsequently adapted to an individual) or on standard (non-custom) earpieces (e.g., earphones), which form parts of hearing instruments 102A, 102B.

Furthermore, in the example of FIG. 1, hearing instrument 102A includes a set of one or more processors 112A. Similarly, in the example of FIG. 1, hearing instrument 102B includes a set of one or more processors 112B. As noted above, computing system 106 may comprise one or more processors 112C. This disclosure may refer to processors 112A, 112B, and 112C collectively as processors 112. Processors 112 may include microprocessors, application-specific integrated circuits (ASICS), digital signal processors (DSPs), field-programmable gate arrays (FPGAs), or other types of processing circuits. Because hearing instruments 102A, 102B, and computing system 106 may be configured to communicate with one another, processors 112 may operate as a processing system 114. Thus, discussion in this disclosure of actions performed by processing system 114 may be performed by one or more processors in one or more of hearing instrument 102A, hearing instrument 102B, or computing system 106, either separately or in coordination.

Processing system 114 may generate information regarding the auditory attention state of user 104 based on one or more EMG signals generated by one or more of electrodes 108 and one or more deformation signals generated by one or more of deformation sensors 110. The auditory attention state of user 104 refers to a state of the user's attention to sounds. The information regarding the auditory attention state of user 104 may include information regarding whether or not user 104 is paying attention to any sounds, a direction toward a current auditory attention locus of user 104 (i.e., a direction toward which user 104 is listening or attempting to listen), a distance to the current auditory attention locus of user 104, a type of sound to which user 104 is listening or attempting to listen, and so on.

As described in this disclosure, processing system 114 may generate information regarding the auditory attention state of user 104 using either or both of (1) pattern recognition or classification algorithms, which categorize the input signal depending on its origin or the user activity to which it corresponds (e.g., jaw movement, opening of the jaw, closing of the jaw, posterior auricular muscle contraction, etc.), and (2) a combination or comparison of signals from at least two sensors placed at different positions within the user's ear. In this example, the sensors may be of the same type (e.g., two deformation sensors or two electrodes) or of different types (e.g., one deformation sensor and one electrode).

Furthermore, processing system 114 may control, based on the information regarding the auditory attention state of user 104, a parameter of the audio system. For instance, the parameter may be an overall volume of one or more of hearing instruments 102. In some examples, processing system 114 controls a directional processing model of hearing instruments 102 based on the information regarding the auditory attention state of user 104. When operating in a directional processing mode, hearing instruments 102 selectively amplify sound originating from a specific direction (e.g., to the front of the wearer, 45 degrees left, 90 degrees left, 45 degrees right, 90 degrees right, etc.) and/or fully or partially cancel sound originating from other directions. In some examples, hearing instruments 102 may reduce noise by canceling out certain frequencies, such as frequencies that are not typically associated with the human voice.

The directional processing mode may help user 104 understand conversations occurring in crowds or other noisy environments. For example, use of a directional processing mode may be useful in a situation in which a hearing-impaired user wears hearing aids equipped with a directional microphone system in an environment containing multiple sound sources, such as multiple talkers. In this situation, it may be advantageous for an algorithm controlling the directional microphone system to have information regarding the direction and/or locus in space where user 104 is attending or wanting to attend. This disclosure may refer to the locus in space where user 104 is attending or wanting to attend as the user's current auditory attention locus.

Furthermore, in some examples, processing system 114 may help user 104 enjoy audio media, such as music or sound components of visual media, by outputting sound based on audio data wirelessly transmitted to processing system 114 (e.g., via one or more audio input sources). In other words, the directional processing mode may be used when a user is listening to sounds (e.g., music, a television program, sounds from a video game) for which it is potentially advantageous to apply different signal processing depending on the user's listening intentions, such as whether user 104 wishes to attend to sounds on the user's right or the left side. A specific instance of this type of situation involves a virtual ('3D') sound system, where different sounds in the simulated acoustic environment can be differentially enhanced, or attenuated, depending on their spatial positions and on the user's listening goals.

In accordance with one or more techniques of this disclosure, processing system 114 uses a deformation signal from at least one deformation sensor (e.g., one of deformation sensors 110) in the ear canal of user 104 to measure deformations of the ear canal and also uses at least one EMG signal from an electrode (e.g., one of electrodes 108) in a concha of user 104 that is configured to measure activity of one or more of the intrinsic auricular muscles of user 104. Using both a deformation signal and an EMG signal representing activity of an intrinsic auricular muscle may be advantageous because outer ear tissue deformations may have many causes, not all of which are relevant to an auditory attention state of user 104 and some of which can be misleading, for the purpose of generating information regarding the user's auditory attention state. Therefore, using mechanical, outer ear deformation signals for the purpose of generating information regarding the user's auditory attention state is likely to produce unreliable practical applications outside of very limited use cases. Conversely, a system that uses only electrodes and EMG signals inside the ear canal, or behind the ear (e.g., on the pinna or mastoid), may be liable to motion artifacts, many of which may be caused by motion of the device or surrounding ear tissues unrelated to auricular muscle activity that is relevant for determining a user's auditory attention state. Example types of motion that may be detected by electrodes inside the ear canal or behind the ear canal that are unrelated to auricular muscle activity may include jaw movements, head motion, or neck muscle activation. These problems can be addressed using certain methods of combined processing of displacement signals measured using a displacement sensor strategically positioned within an ear canal of a user, and EMG signals measured simultaneously using at least one electrode, strategically positioned within a concha of the same user.

In accordance with some examples of this disclosure, at least one of deformation sensors 110A and/or deformation sensors 110B is positioned on the lower, anterior-facing surface of the ear canal, so that the deformation sensor is proximal to the jawbone inside the user's ear canal, so that jaw movements can be reliably detected by the deformation sensor. Moreover, in accordance with examples of this disclosure, at least one electrode (e.g., one or electrodes 108A, electrodes 108B) is placed inside the concha of user 104, and within a few millimeters of at least one intrinsic auricular muscle, so that the electrode can generate an EMG signal representing the activity of this intrinsic auricular muscle.

There are six intrinsic auricular muscles: the transverse, oblique, tragicus, antitragicus, helicis minor, and helicus major. Among the intrinsic auricular muscles, the transverse auricular muscle may be advantageous for applications that seek to determine the azimuthal angle corresponding to the current locus of a user's auditory attention. In other words, the transverse auricular muscle may be used to determine an angle within a horizontal, transverse plane of a direction toward the current auditory attention locus of user 104. Therefore, in some examples, at least one of electrodes 108A and/or electrodes 108B is located within a few millimeters of the left and/or right transverse auricular muscle, in the left and/or right concha of user 104. There is evidence that the activity of the transverse auricular muscle is more closely related to an individual's listening intention, especially where in space user 104 is orienting his/her auditory attention, and may be less influenced by emotions, than the extrinsic posterior periauricular muscle.

Moreover, transverse auricular muscle activity measured using EMG may be related directly and straightforwardly to horizontal eye movements and there is some evidence that the strength of activation of the muscle transverse auricular muscle predicts head-orientation behavior. This physiological property of the transverse auricular muscle may enable processing system 114 to generate information regarding the auditory attention state of user 104 (e.g., a listening intention, a direction toward the current auditory attention locus of user 104, a distance to the current auditory attention locus of user 104, etc.). EMG signals from the transverse auricular muscle appear to be measurable in most individuals, in contrast to EMG signals from the posterior or other extrinsic periauricular muscles, which are more variable in strength across individuals.

In some examples, electrodes 108 include in-concha electrodes that measure EMG responses of the oblique auricular muscle. The oblique auricular muscle may be involved in orienting the pinna along a vertical axis. Accordingly, placement of at least one electrode within a few millimeters of the oblique auricular muscle, in the concha of user 104, may be useful in applications based on a vertical axis, e.g., to emphasize sound sources located below or above the user's line of sight.

Reactions to sound include, but are not limited to, a contraction or other reaction of an intrinsic auricular or periauricular muscle after the onset of a sound. Listening intentions include, for example, whether user 104 is currently listening, or attempting to listen to sound in general (as opposed to visual stimuli), and if so, what sound(s) user 104 wishes to listen to. In this disclosure, the phrase "auditory attention state" refers broadly to any aspect of the user's auditory attentional state, including but not limited to, whether or not user 104 is currently attending to auditory stimulation, which may correspond to sound in the user's acoustic environment or to imagined sound, and where in space that attention is directed e.g., toward the left, the right, the front, or the back, near or far.

In some examples of this disclosure, processing system 114 combine or compare deformation signals indicative of ear canal deformations obtained using two or more of deformation sensors 110. Combining or comparing two or more deformation signals may improve the generation of information regarding the user's auditory attention state. In accordance with such examples, two or more of deformation sensors 110 may be placed at different locations within each ear canal of user 104. In other words, two or more of deformation sensors 110A may be positioned in different locations within a left ear canal of user 104 and two or more of deformation sensors 110B may be positioned in different locations within a right ear canal of user 104. In some examples of this disclosure, one deformation sensor is positioned on a lower anterior surface of the ear canal, adjacent to the jawbone, and a second sensor is positioned on the upper posterior surface of the ear canal.

By comparing deformation signals across these two deformation sensors, processing system 114 can more accurately determine a likelihood that the ear canal deformation is due to a jaw movement, or due to a posterior auricular muscle activation. By comparing the ear canal deformation signals and EMG signals from electrodes 108 positioned in the user's concha(s) to detect activity of one or more intrinsic auricular muscle(s), processing system 114 may determine a likelihood that the EMG signals represent activity of the intrinsic auricular muscle(s) in response to external sounds. In some examples, processing system 114 may determine likelihoods that EMG signals represent activity of a periauricular muscle, a jaw movement, or some other source.

Figure 2:
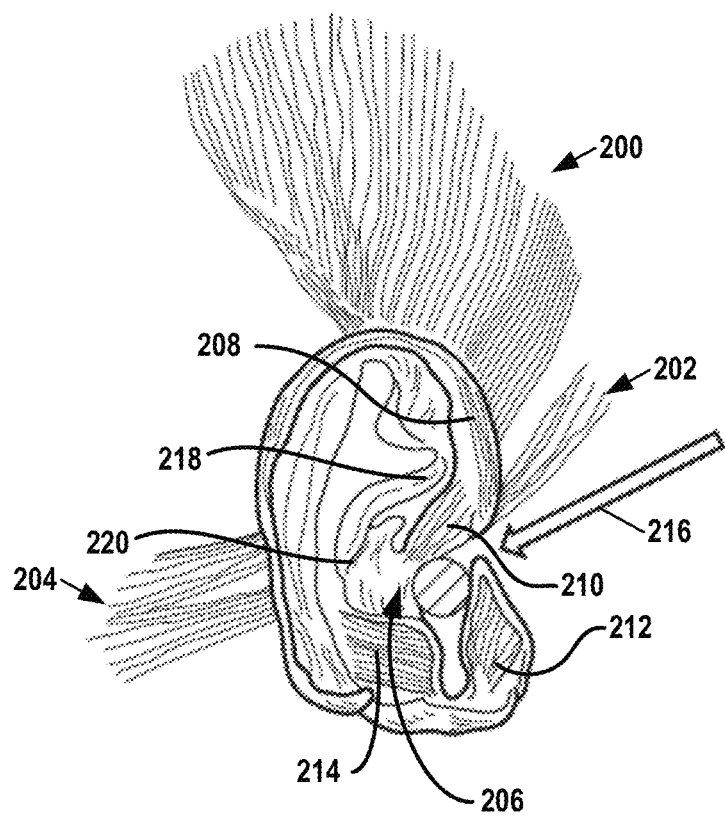
FIG. 2 is a conceptual diagram illustrating muscles of the human ear, along with an example location for wearing of a hearing instrument, in accordance with an example of this disclosure.

FIG. 2 is a conceptual diagram illustrating muscles of the human ear, along with an example location for wearing of a hearing instrument, in accordance with an example of this disclosure. As shown in FIG. 2, muscles of the human ear include extrinsic auricular muscles (i.e., periauricular muscles) and intrinsic auricular muscles. The extrinsic auricular muscles include an auricularis superior muscle 200, an auricularis anterior muscle 202, and an auricularis posterior muscle 204. The ear itself has a concha 206. The intrinsic auricular muscles include a helicis major muscle 208, a helicis minor muscle 210, a tragicus muscle 212, an antitragicus muscle 214, an oblique auricular muscle 218, and a transverse auricular muscle 220. Arrow 216 indicates a location in concha 206 where a hearing instrument configured in accordance with techniques of this disclosure may be worn.

The muscles of the human ear form part of a neuromuscular pinna-orienting and shaping system, which in some animal species is used to swivel the pinna(s) toward spatial locations corresponding to sound sources of interest and adjust a shape of the pinna for optimal hearing of sound sources of interest. In humans, the pinnas are strongly anchored to the skull, making it difficult for most individuals to appreciably move them. Moreover, in humans, the intrinsic muscles of the ear typically are only able to make minimal changes to the shape of the outer ear. However, a few individuals can wiggle their pinnas, albeit feebly compared to felines and other types of animals. Nonetheless, the muscles of the human ear still contract depending on the position and volume of external sounds as well as under volitional orientation of auditory attention, and these contractions, or micro-contractions, can be recorded using electrodes placed on the muscles, such as electrodes 108 (FIG. 1). In addition to being triggered reflexively in response to sound stimulation, some types of contractions of the muscles of the human ear can be elicited voluntarily by user 104. Therefore, signals indicating activity of the muscles of the human ear are candidates for non-intrusively tracking the auditory state of user 104. In some individuals, volitional control of the muscles of human ear can be trained using biofeedback methods.

Figure 3A:
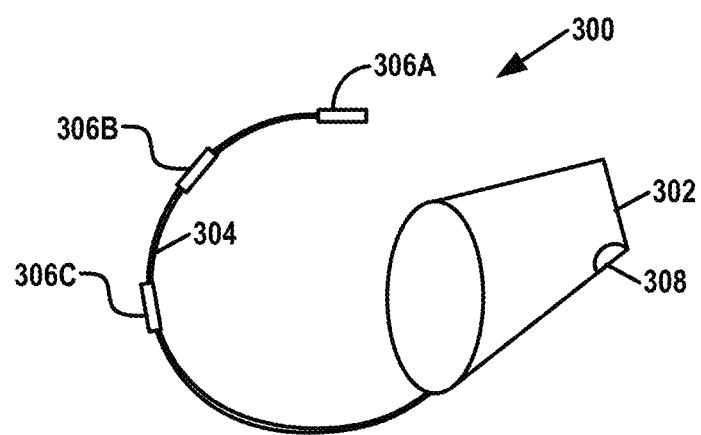
FIG. 3A is a conceptual diagram illustrating an example in-ear hearing instrument that includes an in-canal element and an intra-concha element, in accordance with one or more techniques of this disclosure.
Figure 3B:
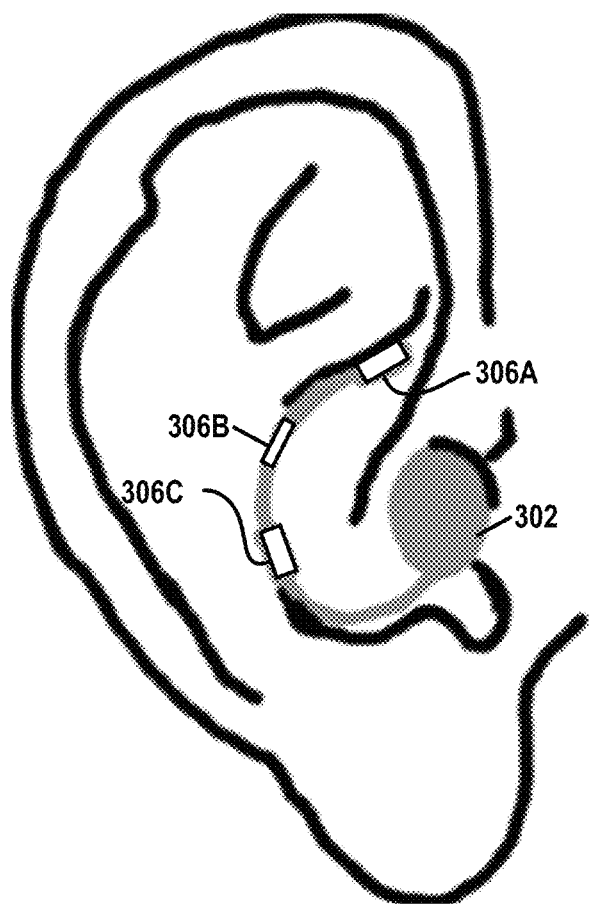
FIG. 3B is a conceptual diagram illustrating the example in-ear hearing instrument of FIG. 3A shown in a user's ear, in accordance with one or more examples of this disclosure.

FIG. 3A is a conceptual diagram illustrating an example in-ear hearing instrument 300 that includes an in-canal element 302 and an intra-concha element 304, in accordance with one or more examples of this disclosure. FIG. 3B is a conceptual diagram illustrating the example in-ear hearing instrument 300 of FIG. 3A shown in a user's ear, in accordance with one or more examples of this disclosure.

In the examples of FIG. 3A and FIG. 3B, in-canal element 302 may be positioned at least partly in an ear canal of a user and may include one or more deformation sensors and/or electrodes. Intra-concha element 304 is positioned and shaped to be worn in a concha of user 104, as shown in FIG. 3B. Intra-concha element 304 comprises one or more electrodes. For instance, in the example of FIG. 3A and FIG. 3B, intra-concha element 304 includes three electrodes 306A, 306B, and 306C (collectively, "electrodes 306"). Electrodes 306 may be examples of electrodes 108A or 108B (FIG. 1).

In some examples, intra-concha element 304 is made of a bio-compatible material (e.g., plastic, silicone, etc.) that is sufficiently flexible to fit comfortably inside the user's concha, but at the same time, is sufficiently rigid to push against the concha with sufficient strength to ensure that electrodes 306 make sufficient contact with the skin to allow reliable measurement of EMG signals.

One or more of electrodes 306 are located on intra-concha element 304 at positions appropriate for detecting EMG signals indicative of activation of one or more intrinsic auricular muscles. In other words, one or more of electrodes 306 may be positioned on a surface of intra-concha element 304 in relation to anatomical landmarks of the user's ear in such a way that one or more of electrodes 306 can be used to measure EMG signals from at least one intrinsic auricular muscle.

For instance, electrode 306C may be positioned on intra-concha element 304, so that electrode 306C faces skin tissues of the concha and is proximal to (and in some examples the middle of) a vertical length of the transverse intrinsic auricular muscle. For instance, electrode 306C may be positioned on a surface of intra-concha element 304 in such a way that electrode 306C makes contact either with an antihelix or with a posterior wall of the concha adjacent to the antihelix (e.g., within a +/−5-millimeter segment centered on a most posterior point on the posterior-pointing bend of the antihelix. In other words, electrode 306C may abut a body of an antihelix of user 104. When electrode 306C is positioned at this location, electrode 306C is likely to be placed over, or close to, the transverse auricular muscle.

In the example of FIG. 3A and FIG. 3B, electrode 306A may measure activity of the oblique auricular muscle. Accordingly, electrode 306A may be configured to be positioned on the posterior surface of the concha adjacent to the antihelix, at a higher location along the antihelix ridge than electrode 306C, and closer to an upper bend of the antihelix. As a result, electrode 306A may be closer to the oblique auricular muscle than to the transverse auricular muscle. Thus, in some examples, processing system 114 may obtain a first EMG signal from electrode 306C positioned to detect activity of the transverse auricular muscle of user 104 and may also obtain a second EMG signal from electrode 306A positioned to detect activity of the oblique auricular muscle of user 104. In such examples, processing system 114 may generate information regarding the auditory attention state of user 104 based on the deformation signal, the first EMG signal, and the second EMG signal. For example, processing system 114 may determine an azimuth angle of a direction toward the user's current auditory attention locus based on the first EMG signal and may determine an elevation angle of the direction toward the user's current auditory attention locus based on the second EMG signal.

Hearing instrument 300 includes a ground electrode, which may be located either on in-canal element 302 or on intra-concha element 304. In the example of FIG. 3A and FIG. 3B, electrode 306B may be a ground electrode. In examples where the ground electrode is located on intra-concha element 304, the ground electrode is at a different position along the length of intra-concha element 304 than the electrode used to measure the EMG signal indicative of activity of the transverse intrinsic auricular muscle. Electrode 306B is located approximately at a midpoint between the locations of electrode 306A and electrode 306C. Locating electrode 306B at the midpoint between the locations of electrode 306A and electrode 306C may optimize the signal-to-noise ratio of EMG signals from the transverse auricular muscle and/or the oblique auricular muscle. In other examples, the ground electrode of hearing instrument 300 is attached to the user's earlobe, is an element worn on the user's ear, outside the user's concha, behind the user's pinna, or on the surface of the skin located above the mastoid bone of user 104. An EMG signal generated by electrode 306A may represent a potential difference between electrode 306A and electrode 306B. Similarly, an EMG signal generated by electrode 306C may represent a potential difference between electrode 306C and electrode 306B.

In the examples of FIG. 3A and FIG. 3B, in-canal element 302 may be positioned at least partly in an ear canal of user 104 and may include one or more deformation sensors and/or electrodes. For instance, in the example of FIG. 3A and FIG. 3B, in-canal element 302 includes a deformation sensor 308. Deformation sensor 308 is positioned and configured to detect deformation of the user's outer ear. For instance, deformation sensor 308 may be positioned and configured to detect deformation of the user's outer ear caused by jaw movements (e.g., jaw movements related to speaking, chewing, or yawning). In such examples, deformation sensor 308 may be positioned on in-canal element 302 such that deformation sensor 308 is positioned on a surface of in-canal element 302 so that deformation sensor 308 faces an anterior-inferior part of the user's ear canal. In a typical user, the user's jaw movements are likely to produce the largest and most easily detectable deformations of the anterior-inferior tissues of the user's ear canal. In some examples, the location of deformation sensor 308 may be at a point of maximum deformation of the user's outer ear caused by movement of the user's jaw.

In some examples, intra-concha element 304 includes one or more deformation sensors in addition to, or in place of, one or more of electrodes 306. For instance, intra-concha element 304 may include one or more displacement sensors, force sensors, optical sensors, or other types of sensors to detect mechanical signals indicative of activation of the transverse intrinsic auricular muscle. Thus, in some examples, the deformation signals may include a deformation signal indicative of deformation of the outer ear of user 104 caused by a transverse auricular muscle of user 104. In such examples, one or more deformation sensors located at least partly inside the concha of user 104 include a sensor configured to generate the deformation signal indicative of deformation of the outer ear of user 104 caused by a transverse auricular muscle of user 104.

Figure 4:
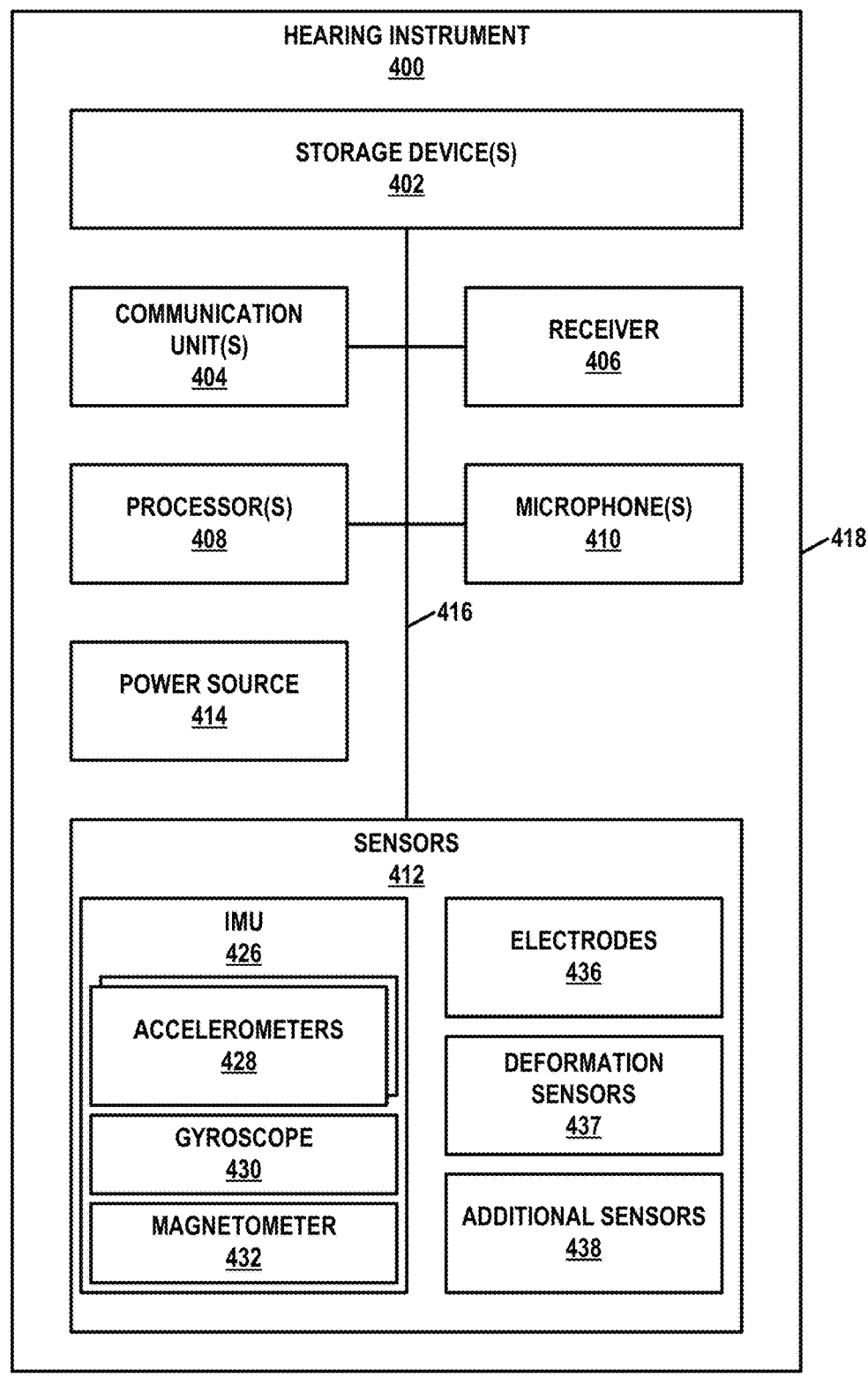
FIG. 4 is a block diagram illustrating example components of a hearing instrument, in accordance with one or more examples of this disclosure.

FIG. 4 is a block diagram illustrating example components of hearing instrument 400, in accordance with one or more examples of this disclosure. Hearing instrument 400 may be either one of hearing instruments 102 (FIG. 1) or hearing instrument 300 (FIG. 3). In the example of FIG. 4, hearing instrument 400 comprises one or more storage devices 402, one or more communication unit(s) 404, a receiver 406, one or more processor(s) 408, one or more microphone(s) 410, a set of sensors 412, a power source 414, and one or more communication channels 416. Communication channels 416 provide communication between storage devices 402, communication unit(s) 404, receiver 406, processor(s) 408, microphone(s) 410, and sensors 412. Components 402, 404, 406, 408, 410, 412, and 416 may draw electrical power from power source 414.

In the example of FIG. 4, each of components 402, 404, 406, 408, 410, 412, 414, and 416 are contained within a single housing 418. However, in other examples of this disclosure, components 402, 404, 406, 408, 410, 412, 414, and 416 may be distributed among two or more housings. For instance, in an example where hearing instrument 400 is a RIC device, receiver 406 and one or more of sensors 412 may be included in an in-ear housing separate from a behind-the-ear housing that contains the remaining components of hearing instrument 400. In such examples, a RIC cable may connect the two housings.

Furthermore, in the example of FIG. 4, sensors 412 include an inertial measurement unit (IMU) 426 that is configured to generate data regarding the motion of hearing instrument 400. IMU 426 may include a set of sensors. For instance, in the example of FIG. 4, IMU 426 includes one or more of accelerometers 428, a gyroscope 430, a magnetometer 432, combinations thereof, and/or other sensors for determining the motion of hearing instrument 400.

Furthermore, in accordance with one or more examples of this disclosure, sensors 412 include one or more electrodes 436 and one or more deformation sensors 436. Electrodes 436 include at least one electrode (e.g., one of electrodes 108 (FIG. 1), electrodes 306 (FIG. 3A, 3B)) that is configured to be positioned in a concha of user 104 and configured to detect activity of an intrinsic auricular muscle of user 104. Deformation sensors 437 may include at least one deformation sensor (e.g., one of deformations sensors 110 (FIG. 1), deformation sensor 308 (FIG. 3A)) that is configured to generate a deformation signal indicative of a deformation of an ear of the user of hearing instrument 400.

In the example of FIG. 4, hearing instrument 400 may also include one or more additional sensors 438. Additional sensors 438 may include a photoplethysmography (PPG) sensor, blood oximetry sensors, blood pressure sensors, electrocardiograph (EKG) sensors, body temperature sensors, electroencephalography (EEG) sensors, environmental temperature sensors, environmental pressure sensors, environmental humidity sensors, skin galvanic response sensors, and/or other types of sensors. In other examples, hearing instrument 400 and sensors 412 may include more, fewer, or different components.

Storage devices 402 may store data. Storage devices 402 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage devices 402 may further be configured for long-term storage of information as non-volatile memory space and retain information after power on/off cycles. Examples of non-volatile memory configurations may include flash memories, or forms of electrically programmable memories (EPROM) or electrically erasable and programmable (EEPROM) memories.

Communication unit(s) 404 may enable hearing instrument 400 to send data to and receive data from one or more other devices, such as a device of computing system 106 (FIG. 1), another hearing instrument, an accessory device, a mobile device, or another type of device. Communication unit(s) 404 may enable hearing instrument 400 to use wireless or non-wireless communication technologies. For instance, communication unit(s) 404 enable hearing instrument 400 to communicate using one or more of various types of wireless technology, such as a BLUETOOTH™ technology, 3G, 4G, 4G LTE, 5G, ZigBee, WI-FI™, Near-Field Magnetic Induction (NFMI), ultrasonic communication, infrared (IR) communication, or another wireless communication technology. In some examples, communication unit(s) 404 may enable hearing instrument 400 to communicate using a cable-based technology, such as a Universal Serial Bus (USB) technology.

Receiver 406 comprises one or more speakers for generating audible sound. Microphone(s) 410 detects incoming sound and generates one or more electrical signals (e.g., an analog or digital electrical signal) representing the incoming sound.

Processor(s) 408 may comprise processing circuits configured to perform various activities. For example, processor(s) 408 may process acoustic signal generated by microphone(s) 410 or synthetic sound sources to enhance, amplify, or cancel-out particular channels within the acoustic signal. Processor(s) 408 may then cause receiver 406 to generate sound based on the processed acoustic signal. In some examples, processor(s) 408 include one or more digital signal processors (DSPs). In some examples, processor(s) 408 may cause communication unit(s) 404 to transmit one or more of various types of data. For example, processor(s) 408 may cause communication unit(s) 404 to transmit data to computing system 106. Furthermore, communication unit(s) 404 may receive audio data from computing system 106 and processor(s) 408 may cause receiver 406 to output sound based on the audio data.

Figure 5:
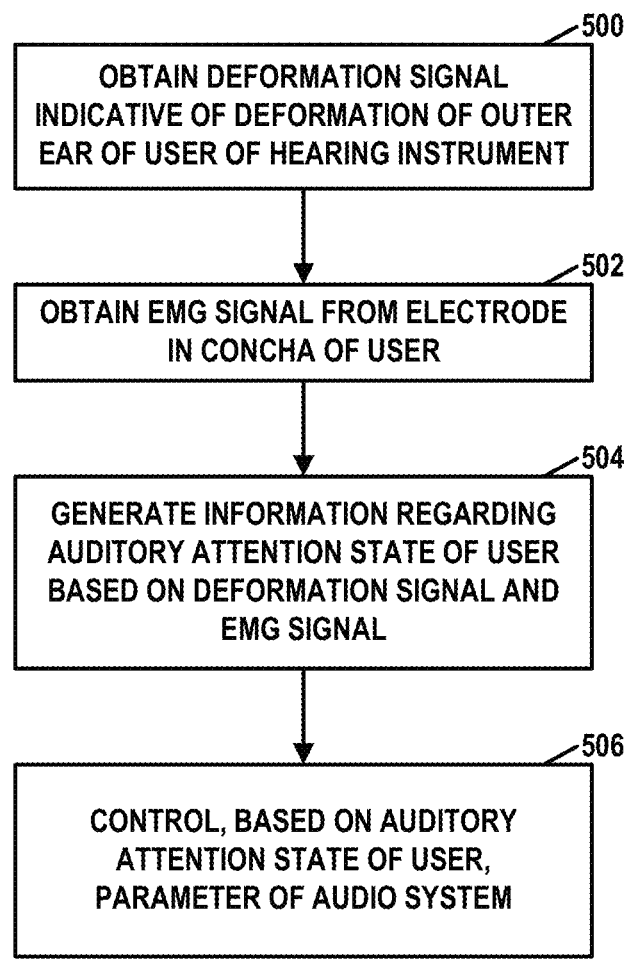
FIG. 5 is a flowchart illustrating an example operation of a processing system, in accordance with one or more examples of this disclosure.

FIG. 5 is a flowchart illustrating an example operation of processing system 114, in accordance with one or more examples of this disclosure. The flowcharts of this disclosure are provided as examples. Other examples of this disclosure may include more, fewer, or different actions.

In the example of FIG. 5, processing system 114 obtains a deformation signal generated by a deformation sensor (500). The deformation signal is indicative of a deformation of an outer ear of a user of a hearing instrument. In addition, processing system 114 obtains an EMG signal generated by an electrode in a concha of user 104 (502). The electrode is configured to detect activity of an intrinsic auricular muscle of user 104. For instance, the EMG signal generated by the electrode may indicate differences in potential between the electrode and another electrode (e.g., a ground electrode, such as electrode 306B (FIGS. 3A, 3B)). In other words, the EMG signal may be indicative of activity of the intrinsic auricular muscle of user 104. Processing system 114 may obtain the deformation signal and the EMG signal in one or more ways. For instance, processing system 114 may receive the deformation signal directly from the deformation sensor and/or the EMG signal directly from the electrode. In some examples, processing system 114 may receive the deformation signal and/or the EMG signal from one or more separate devices (e.g., from hearing instrument 102A or hearing instrument 102B).

Furthermore, in the example of FIG. 5, processing system 114 may generate information regarding an auditory attention state of user 104 based on the deformation signal and the EMG signal (504). Example types of information regarding the auditory attention state of user 104 may include information regarding reactions of user 104 to sounds, the listening intentions of user 104, the direction toward the current auditory attention locus of user 104, and so on. In contrast to determining information about the direction toward the current auditory attention locus of user 104, determining information about the listening intentions of user 104 may include determining (e.g., based on the deformation signal and EMG signal being different from a previous deformation signal and EMG signal) that user 104 wants to change listen to a different sound source than before. In some examples, processing system 114 may generate information indicating a distance to an auditory attention locus of user 104. Examples of how processing system 114 may generate information regarding the direction toward the user's current auditory attention locus are provided elsewhere in this disclosure.

As noted above, processing system 114 may generate information regarding the auditory attention state of user 104. In some examples, processing system 114 may use deformation signals and EMG signals from sensors in left and right ears of user 104 to generate information regarding the auditory attention state of user 104. Processing system 114 may perform comparisons of the displacement and EMG signals measured by the sensors in the left ear and the sensors in the right ear of user 104 to generate information regarding the auditory attention state of user 104. For example, processing system 114 may combine left and right-ear ear canal deformation and concha EMG signals to more precisely determine an angle corresponding to a direction or distance of a current auditory attention locus of user 104.

In some examples, processing system 114 combines measures of ear canal deformations obtained using at least one deformation sensor in the ear canal, and EMG signals measured using at least one electrode in a concha of user 104, with additional sensors, including, but not limited to, electrodes, microphones, gyroscopes, and accelerometers. For instance, in some examples, one deformation sensor (e.g., a displacement, pressure or force sensor) measuring ear canal deformations, and one electrode measuring auricular EMG signals (where the electrode may be referenced to a ground electrode in the concha or elsewhere), are placed in each of the left and right ear canals of user 104, and the measured ear canal deformation signals are combined with the auricular EMG signals across the two ears, to potentially improve the reliability of the detection or classification of a user's auditory reactions to sound, auditory attentional state, or listening intentions.

In some examples, processing system 114 combines ear canal deformation signals measured using at least one deformation sensor with EEG or EOG signals to potentially improve the generation of information regarding the auditory attention state of user 104. Although EEG or EOG signals can be measured inside the user's ear canal, and can provide information regarding one or more aspects of the user's auditory attention state (e.g., the user's auditory reactions to sound, direction toward the current auditory attention locus of user 104, or listening intentions), these signals are susceptible to contamination by interference sources located in the user's environment (e.g., power lines, electronic equipment, etc.) or in the user's body (e.g., other muscles or neurons than those of primary interest). Among the source of interference in the user's body, movements of the jaw, neck, or head all have the potential to generate artifacts or spurious signals, which can pollute or mask EEG or EOG signals measured inside the ear canal, especially when these signals are measured using dry electrodes, which require a stable electrode-skin interface; the impedance and other aspects of the electrode-skin interface can vary sharply during momentary deformations of the ear canal. In this context, use of a deformation signal and an EMG signal from an in-concha electrode may improve generation of information regarding the user's auditory attention state (e.g., the user's reactions to sound, direction toward the current auditory attention locus of user 104, or listening intentions), beyond what may be achieved using EEG or EOG signals alone. For example, the detection of an ear canal deformation event during the measurement of an EEG or EOG signal by one or more electrodes placed in, on, or around the ear, can inform the interpretation or classification of this EEG or EOG signal (e.g., by signaling the likely presence of a movement-related artifact in this signal).

In some examples, processing system 114 uses deformation sensors to detect jaw movements, and uses information regarding the jaw movements to improve the processing of EMG signals for the purpose of improving the detection or classification of EMG signals that are specifically indicative of a user's auditory reactions, auditory attention, or listening intentions. In some examples, the processing of deformation signals in relation to EMG signals involves stopping further processing of the EMG signal while signals indicative of jaw movement are detected by the deformation sensor, thereby saving computational and electrical power resources of hearing instruments 102. Thus, in some examples, processing system 114 may determine, based on the deformation signal, whether the deformation of the ear of user 104 was caused by a movement of a jaw of user 104. When the deformation of the ear of user 104 was not caused by the movement of the jaw of user 104, processing system 114 may generate, based on the EMG signal, the information regarding the auditory attention state of user 104. Conversely, when the deformation of the ear of user 104 was caused by the movement of the jaw of user 104, processing system 114 may refrain from generating information about the auditory attention state of user 104 based on the EMG signal.

In some examples, processing system 114 may classify the deformation signals as belonging to a jaw movement class (i.e., determine that the deformation signal is indicative of a movement of the user's jaw) based on a comparison of the magnitudes (or 'strengths') of sensor signals across two or more sensors. In some such examples, at least one of the sensors is located on the anterior lower part of the user's ear canal and at least one of the sensors is located on the posterior upper part of the user's ear canal. Furthermore, in such examples, the classifier may determine that the sensor signals belong to a class of jaw movement signals when the strength of the signal generated by the lower anterior sensor is greater than the strength of the signal generated by the upper posterior sensor.

Conversely, processing system 114 may determine that the deformation signal belongs to a class of periauricular muscle signals when the strength of the signal generated by an upper-posterior deformation sensor is greater than the strength of the signal generated by the lower-anterior deformation sensor. In some examples where processing system 114 classifies deformation signals based on a combination of two or more deformation signals, the classification of the deformation signals may be more accurate than can be achieved using a single deformation sensor. The deformation sensors may be of the same type, or of different types. These deformation sensors may occupy different positions within the ear canal or concha of user 104 and these positions may be chosen to minimize or reduce the likelihood of misclassifications.

The classification of deformation signals into a class of jaw movement signals may be further aided by analyses of temporal properties of one or more of the sensor signals. For example, the deformation signals induced by jaw movements during chewing typically have different statistical temporal properties than sensor signals measured during speaking. For example, pulses of deformation of the user's outer ear occur during both chewing and eating. However, the rates at which the pulses of deformation of the user's outer ear occurs may be different for chewing and eating.

In some examples where processing system 114 classifies the sensor signals into various classes of jaw movement signals, processing system 114 may perform a modulation-frequency-power analysis. As part of performing the modulation-frequency-power analysis, processing system 114 may detect the statistical temporal properties by computing a temporal envelope of the sensor signals. Computation of the temporal envelope of the sensor signals can be achieved, for example, using an electronic circuit or digital device that performs half-wave rectification followed by lowpass filtering. Additionally, as part of performing the modulation-frequency-power analysis, processing system 114 may perform a frequency analysis (e.g., a fast Fourier transform (FFT)) of the temporal envelope. Processing system 114 may compute the FFT using a specialized digital signal-processing circuit or a general-purpose computer processor, such as a processor included in a smartphone. Furthermore, as part of performing the modulation-frequency-power analysis, processing system 114 may measure an absolute or relative amplitude (i.e., power) of envelope-frequency components within a frequency range corresponding to speech (e.g., 3-16 Hz) and/or in a frequency range corresponding to chewing (e.g., 0.5-3 Hz). Processing system 114 may use the results of the modulation-frequency-power analysis to classify jaw movements into a chewing class versus a speaking class.

In some examples, processing of deformation signals in relation to EMG signals from electrodes in the concha involves using certain characteristics of the measured deformation signal, such as a shape of the deformation signal, to decompose the EMG signal into two components: a first component related to the deformation signal and corresponding to an electrical artifact of jaw movement, and a second component unrelated to the deformation signal. Processing system 114 may further process the second component (i.e., the component of the EMG signal unrelated to deformation of the user's ear) to determine information regarding the auditory attention state of user 104, such as an auditory reaction of user 104, auditory attention, listening intention, direction of the user's current auditory attention locus, and so on. In such examples, processing system 114 may use the second component as the EMG signal as described elsewhere in this disclosure to determine the information regarding the auditory attention state of user 104.

In some examples, to decompose the EMG signal into the first component and the second component, processing system 114 may implement an example of deconvolution that involves filtering the measured EMG signal into two different frequency bands: a low frequency band (e.g., using a lowpass filter with a cutoff frequency of between 2 and 10 Hz) corresponding to the deformation signal, and a higher frequency band (e.g., using a bandpass filter with a lower cutoff frequency of about 5 Hz and an upper cutoff frequency of about 400 Hz) corresponding to the EMG component unrelated to the deformation signal.

In another example of how processing system 114 may decompose the EMG signal into the first component and the second component, processing system 114 may subtract a model artifact deformation signal (which may be stored in a memory) from the measured EMG signal. The model artifact deformation signal may serve as a template. The model artifact deformation signal (or pattern) could have been learned beforehand, for example, by recording and averaging together EMG signals measured during repeated opening and closing of the jaw by the user, in a manner not unlike the measurement of fingerprints during the initialization process for a new mobile phone.

Furthermore, in some examples, processing system 114 may decompose the EMG signal using signals measured using additional sensors, such as a microphone on one of hearing instruments 102, to measure own-voice speech signals from the user, and then use some characteristic (e.g., temporal envelope) of such signals to "subtract out" the speech-related jaw deformation component from the EMG signal, leaving only a signal that is unrelated to the deformation of the jaw.

Additionally, in the example of FIG. 5, processing system 114 may control, based on the information regarding the auditory attention state of user 104, a parameter of audio system 100 (506). Example parameters of audio system 100 may include whether directional processing is active, a direction for directional processing, a global gain for audio system 100, whether or not particular operating modes of audio system 100 are active or inactive, and so on. Thus, based on the information regarding the auditory attention state of user 104, processing system 114 may activate a directional processing mode, change a volume of one or more of hearing instruments 102 or control other aspects of audio system 100 based on the information regarding the auditory attention state of user 104. The parameters of audio system 100 may control or describe aspects of how audio system 100 processes acoustic signals generated by microphones or synthetic sound sounds. Thus, in the case where audio system 100 processes acoustic signals generated by synthetic sound sources, processing system 114 may determine, based at least in part on auricular EMG signals generated in the concha of user 104 while user 104 is playing a video game (with synthesized sounds) or listening to synthetic music, a direction toward which of the sounds playing at a given moment the user's auditory attention is being directed. Processing system 114 may use the resulting information, for instance, to selectively increase the volume of said sound (or decreasing the volume of other sounds) to facilitate its auditory detection by user 104.

Generating information regarding the user's auditory attention state may be useful in various applications, such as the control of an audio system, such as audio system 100 (FIG. 1). As described elsewhere in this disclosure, audio system 100 may include one or more devices configured to generate or process sound, including, but not limited to, sound-recording systems, earphones, headphones, loudspeakers, sound amplifiers, and hearing aids. Information regarding a user's auditory attention state can be used advantageously to set or adjust certain parameters of audio system 100. For example, processing system 114 may use the information regarding the user's auditory attention state to turn up the volume of sounds to which user 104 currently wants to listen, or to turn down the volume of sounds to which user 104 does not wish to listen. Because the user's listening intentions may change rapidly over time, it is not usually practical for user 104 to have to indicate manually, whenever his/her listening intentions change. In this context, it may be advantageous for processing system 114 to continuously or frequently generate information regarding the user's auditory attention state as the user's auditory attention state changes.

In some examples where the information regarding the user's current auditory attention locus includes information indicating a distance to the user's current auditory attention locus, processing system 114 may control the parameter of audio system 100 based on the distance to the user's current auditory attention locus. In some examples where the information regarding the user's current auditory attention locus includes information indicating both a direction toward the user's current auditory attention locus and a distance to the user's current auditory attention locus, processing system 114 may control the parameter of audio system 100 based on both the direction toward the user's current auditory attention locus and the distance to the user's current auditory attention locus.

Processing system 114 may use information indicating the distance to the user's current auditory attention locus in any of a variety of ways. For instance, in one example, processing system 114 may use a distance estimate of a sound source relative to user 104 to control a pair of directional microphones, involving one directional microphone on the right side of the user's head, and one directional microphone on the left side of the user's head. Specifically, the left- and right-side directional microphones may be programmed so that the left- and right-side directional microphones have beams pointing in different directions, with these directions chosen (based on the distance estimate) to reinforce selectively sounds coming from said direction. Another example may involve listening to sound recordings through an audio listening device (e.g., headphones). In this example, having an estimate of the perceived distance of certain sounds in the streamed recording (e.g., a musical instrument in a polyphonic music recording), which a user is listening to, could be used to selectively reinforce (i.e., increase the sound level) of that instrument. This is analogous to the previous example, except that it applies to recorded music.

Yet another example involves combining the distance estimate obtained by processing auricular muscle signals, with another distance estimate, obtained by processing microphone signals (e.g., acoustic environment analysis). For example, the former distance estimate (from EMG) could be compared with the latter (from audio processing) to determine which, among several different sound sources in the environment, a user is wanting to listen to.

Figure 6:
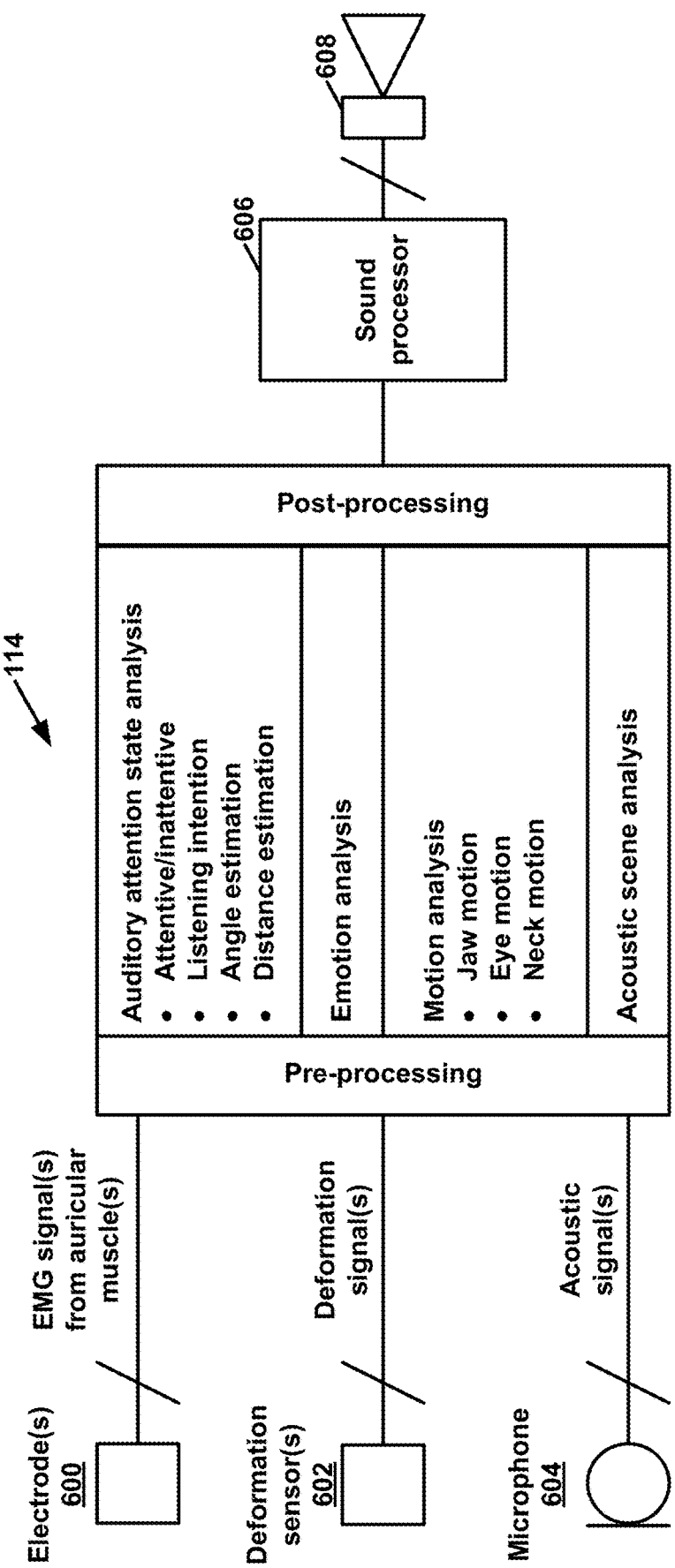
FIG. 6 is a conceptual diagram illustrating an example processing scheme, in accordance with one or more examples of this disclosure.

FIG. 6 is a conceptual diagram illustrating an example processing scheme, in accordance with one or more examples of this disclosure. In the example of FIG. 6, processing system 114 receives signals generated by a plurality of sources. In the example of FIG. 6, these sources include a set of one or more electrodes 600, a set of one or more deformation sensors 602, and a set of one or more microphones 604.

Electrodes 600 may include one or more electrodes (e.g., electrodes 306 (FIG. 3A and FIG. 3B)) that are positioned in one or more conchae of user 104 and that are configured to detect activity of one or more intrinsic auricular muscles of user 104. Furthermore, in some examples, electrodes 600 may further include one or more electrodes configured to measure electroencephalography (EEG) or electrooculography (EOG) signals of user 104. In some examples, one or more of the electrodes configured to measure EEG or EOG signals are positioned on one or more of in-canal element 302 or intra-concha element 304. In some examples, one or more of the electrodes configured to measure EEG or EOG signals are separate from any hearing instrument. For instance, in some examples, one or more of the electrodes configured to measure EEG or EOG signals are located in a head-worn device, such as a hat or cap, glasses, eye-worn devices (e.g., contact lenses), or other types of devices. Thus, in some examples, processing system 114 may obtain an additional signal generated by an additional sensor, wherein the additional signal is an EEG signal or an EOG signal. In such examples, processing system 114 may generate the information regarding the auditory attention state of user 104 based on the EMG signal, the deformation signal, and the additional signal.

In the example of FIG. 6, deformation sensors 602 include a deformation sensor (e.g., deformation sensor 308) positioned at an anterior-inferior surface of the ear canal of user 104. Furthermore, in some examples, deformation sensors 602 may include one or more additional deformation sensors. For instance, in one example, in-canal element 302 may include one or more deformation sensors that are configured to be positioned inside the user's ear canal in order to measure deformations of the user's ear canal that relate to other anatomic regions than the lower-anterior region of the ear canal. For example, an additional deformation sensor may be positioned on a posterior-facing region of in-canal element 302. The deformation sensor positioned on the posterior-facing region of in-canal element 302 may be conducive to the detection of ear canal deformations caused by activity of the posterior periauricular muscle (e.g., the auricularis posterior muscle 204 (FIG. 2)). In some examples, an additional deformation sensor may be positioned on a superior-facing region of in-canal element 302. The deformation sensor positioned on the superior-facing region of in-canal element 302 may be conducive to the detection of ear canal deformations caused by activity of the superior periauricular muscle (e.g., auricularis superior muscle 200 (FIG. 2)).

Processing system 114 may generate information regarding the auditory attention state of user 104 based on deformation signals, EMG signals from one or more electrodes in a concha of user 104, and one or more EEG and/or EOG signals. For instance, processing system 114 may generate information regarding an auditory reaction, auditory attentional state, or listening intention based on deformation signals, EMG signals from one or more electrodes in a concha of user 104, and one or more EEG and/or EOG signals.

Furthermore, in the example of FIG. 6, processing system 114 may receive one or more acoustic signals (e.g., from one or more microphones 604, from a sound synthesis system, from a communication link, or another source). Microphones 604 may be examples of microphones 410 (FIG. 4). The sound synthesis system may comprise one or more processors, which may be part of or separate from processing system 114, that may generate an artificial acoustic signal. Processing system 114 may process the acoustic signals to detect or classify one or more aspects of an acoustic environment (e.g., a natural or artificial acoustic environment) of user 104. For example, processing system 114 may determine whether specific types of sounds are present in the acoustic environment (e.g., speech, approaching vehicles, etc.), a sound level or intensity of specific sounds in the acoustic environment, approximate locations (e.g., real or virtual locations) of sound sources relative to user 104. Processing system 114 may use the results of processing the acoustic signals to inform the processing of signals measured by other sensors (e.g., electrodes 600, deformation sensors 602, etc.).

For instance, in one example, processing system 114 may determine (e.g., based on sound level and/or sound direction information, deformation signals generated by deformation sensors 602 and also EMG signals generated by electrodes 600) a likelihood that the deformation signals generated by deformation sensors 602 and the EMG signals generated by electrodes 600 represent auditory reactions of user 104 to external sounds. In this example, if the likelihood is greater than a specific threshold, processing system 114 may determine that the deformation signals and EMG signals represent an auditory reaction of user 104 to an external sound.

In one example of how processing system 114 may determine the likelihood that the EMG signals generated by electrodes 600 are indicative of activity of one or more intrinsic auricular muscles in response to external sounds, processing system 114 may compare the time of occurrence of an acoustic event, such as a sound onset, and certain features or events in the deformation signal and EMG signals. An example event may be the crossing of a threshold by either or both the EMG signal and the deformation signal. If the features or events detected in the deformation signal and the EMG signal occurred within a critical period (e.g., within less than 300 milliseconds) after the acoustic event, processing system 114 may determine a higher likelihood that the deformation signal and the EMG signal represent auditory reactions of user 104 to the acoustic event if the feature or event detected in the deformation signal and the EMG signal occurred after the critical period (e.g., 300 milliseconds or more after the acoustic event) than if the feature or event detected in the deformation signal and the EMG signal occurred before the acoustic event.

As another example of a use of a combination of acoustic signals with deformation signals and EMG signals, once processing system 114 has determined that the deformation signal and/or EMG signal represent an auditory reaction to an acoustic event in the user's environment, processing system 114 may generate information regarding one or more relationships between one or more aspects of the deformation signal, one or more aspects of the EMG signal, and one or more aspects of the acoustic event. For example, processing system 114 may determine a spatial location of the sound source that generated the acoustic event in relation to the location of user 104. In this example to determine the spatial location of the sound source that generated the acoustic event, processing system 114 may estimate a direction toward the current auditory attention locus of user 104 based on the acoustic signals (e.g., using one or more head-related transfer functions). Furthermore, in this example, processing system 114 may estimate a direction toward the current auditory attention locus of user 104 based on the EMG signals. In this example, processing system 114 may compare the direction of the sound source relative to user 104, and the direction toward the current auditory attention locus of user 104. For instance, processing system 114 may implement a logic gate that controls the activation of further processing based on a difference between the angle of the sound source and the angle toward the user's current auditory attention locus. For example, processing system 114 may perform different actions based on whether the difference is positive, or negative, or whether a magnitude of the difference is within or outside of a margin of error. For example, if the magnitude of the difference is larger than a margin of error, processing system 114 may perform a calibration or recalibration process, whereby variables used in the computation of an angle of attention by processing system 114 are adjusted, such that subsequent estimates of the angle of attention by processing system 114, fall within the margin of error of the computed angle of the sound source.

In some examples, processing system 114 may perform an emotion analysis based at least in part on the EMG signals and deformation signals. As noted above, responses of particular auricular muscles (e.g., the posterior auricular muscle) may be modulated in some individuals depending on the emotional states of the individuals. In other words, the level of activation of specific intrinsic auricular muscles and/or periauricular muscles in response to the same sounds may be different, depending on the individual's emotional state. For example, specific auricular muscles may exhibit greater activity in response to the same sound in an individual when user 104 is stressed than when user 104 is relaxed.

Performing the emotion analysis may include determining an emotional state of user 104. To determine the emotional state of user 104, processing system 114 may compare a current activation level of an intrinsic auricular muscle in response to a detected acoustic signal (including direction, distance, loudness, type, etc. of the acoustic signal) to activation levels of the intrinsic auricular muscle in response to similar, previously detected acoustic signals. The previously detected acoustic signals may be mapped to emotional states of user 104. Based on this comparison, processing system 114 may identify one of the previously detected acoustic signals that is associated with an activation level of the intrinsic auricular muscle that is closest to the current activation level of the intrinsic auricular muscle. Processing system 114 may then determine that user 104 currently has the emotional state associated with the identified previously detected acoustic signal.

As shown in the example of FIG. 6, processing system 114 may perform post-processing. For example, processing system 114 may control, based on the information regarding the auditory attention state of user 104, the parameter of audio system 100. Processing system 114 may control the parameter of audio system 100 in accordance with any of the examples provided elsewhere in this disclosure. Furthermore, in the example of FIG. 6, a sound processor 606 may modify acoustic signals in accordance with the parameter of audio system 100. For instance, in an example where the parameter is whether or not a directional processing mode is active in audio system 100, sound processor 606 may increase the amplitude of sounds arriving from particular directions while attenuating sounds arriving from other directions depending on the parameter. Sound processor 606 may be implemented as part of processing system 114 (e.g., as part of processor(s) 408 (FIG. 4)). Receivers 608 may output sound represented by the modified acoustic signals. Receivers 608 may include receiver 406 (FIG. 4).

Figure 7:
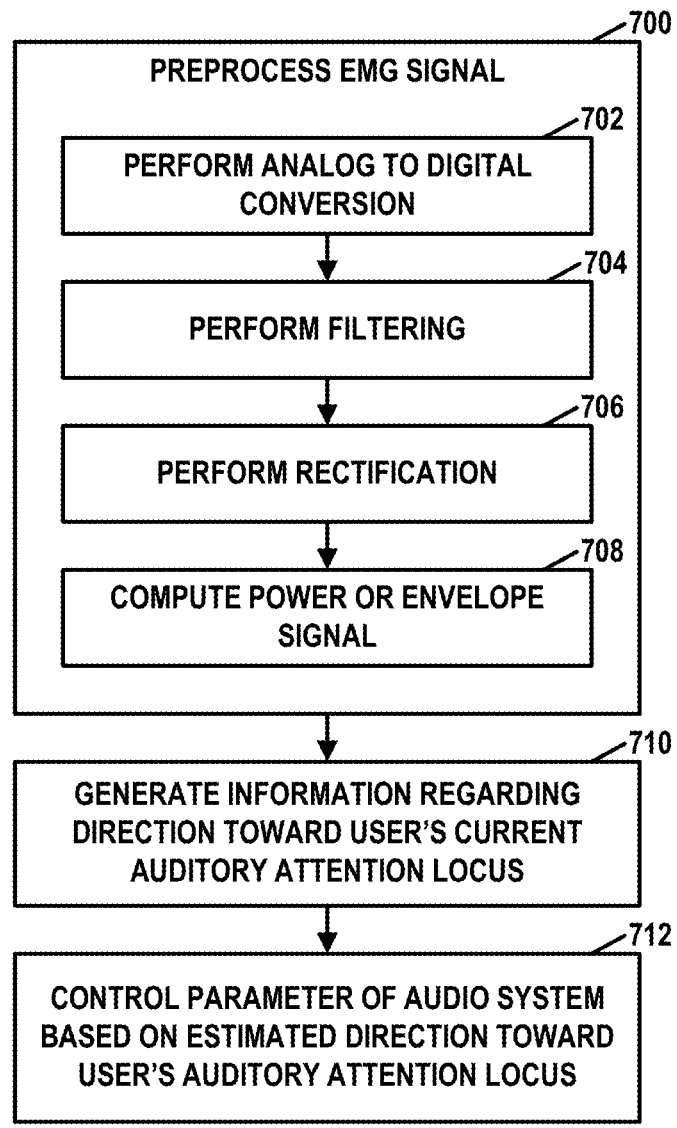
FIG. 7 is a flowchart illustrating an example operation of a processing system in which the processing system obtains an electromyography (EMG) signal from an electrode configured to detect activity of a transverse auricular muscle.

FIG. 7 is a flowchart illustrating an example operation of processing system 114 in which processing system 114 obtains an EMG signal from an electrode configured to detect activity of a transverse auricular muscle. In other words, where electrodes 600 (FIG. 6) include an electrode located close to the transverse auricular muscle, processing of the EMG signal from this electrode may include steps shown in the example of FIG. 7.

In the example of FIG. 7, processing system 114 may preprocess the EMG signal (700). As part of preprocessing the EMG signal, processing system 114 may perform an analog-to-digital (A/D) conversion of the EMG signal (702). In addition, processing system 114 may perform a filtering process on the digital EMG signal (704). For example, processing system 114 may apply one or more of a low-pass filter (e.g., a filter with a cutoff frequency between 40 and 400 Hz), a high-pass filter (e.g., a filter with a cutoff frequency between 0.1 and 10 Hz), a band-pass filter (e.g., a filter combining the low-pass and high-pass filters previously described), or a band-rejection filter (e.g., using a rejection frequency band centered on a power-line frequency or multiple thereof). Processing system 114 may apply the filtering process for artifact removal (e.g., power-line removal) in the EMG signal and/or to improve the signal-to-noise in the EMG signal.

Furthermore, in the example of FIG. 7, processing system 114 may perform a rectification process on the filtered EMG signal (706). For example, processing system 114 may perform full-wave or half-wave rectification on the filtered EMG signal. Additionally, processing system 114 may compute a power or envelope signal of the rectified EMG signal (708). Processing system 114 may apply low-pass, high-pass, or band-pass filtering, moving-averaging, or convolution of the rectified signal with a temporal window shape, such as a Hamming window, for the purpose of computing the power or envelope signal. Processing system 114 may use the power or envelope signal as an estimate of the activation strength of an auricular muscle.

Processing system 114 may use the signal strength estimate computed in the preceding step to generate information regarding a direction toward the user's current auditory attention locus (710). As discussed elsewhere in this disclosure, user 104 may change the user's auditory attention locus of their own volition or may reflexively change the user's auditory attention locus as a reaction to a sound that user 104 heard. Examples of how processing system 114 may use the signal strength estimate to generate the information regarding the direction toward the user's current auditory attention locus are provided elsewhere in this disclosure.

Furthermore, in the example of FIG. 7, processing system 114 may control one or more parameters of audio system 100 based on the estimated direction toward the user's current auditory attention locus (712). For example, processing system 114 may generate a command signal that activates a directional processing mode based on the direction toward the current auditory attention locus of user 104, changes volume of one or more hearing instruments, or controls other actions.

Processing system 114 may estimate the direction toward the user's current auditory attention locus in one of a variety of ways. For example, an angle of attention may be computed based on a transverse auricular muscle signal strength estimate obtained on the left side (left ear) of the user's head, using the following equation, $$a_l = (-\ln(1/t_l - 1) + b)/c \quad \text{(Eq. 1)}$$

Figure 8A:
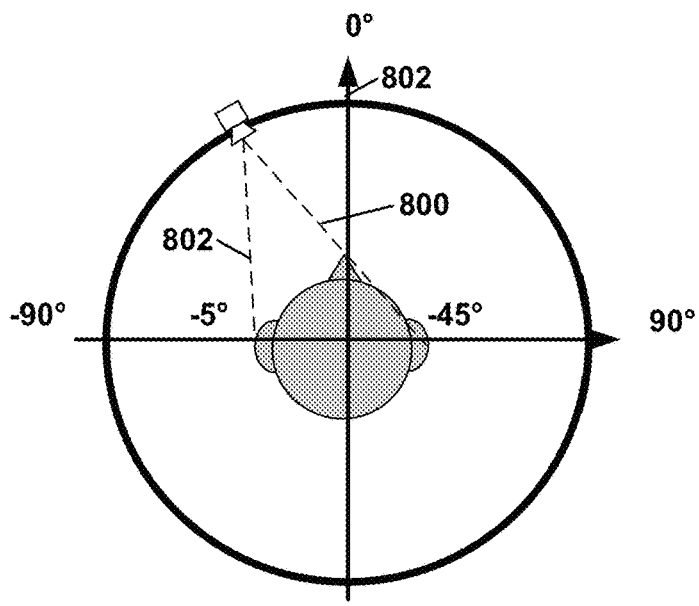
FIG. 8A is a conceptual diagram illustrating an example of determining a direction toward a current auditory attention locus of a user, in accordance with an example of this disclosure.

In Eq. 1, $\ln(\cdot)$ denotes the natural logarithm function and $a_l$ is the computed angle of attention (in degrees, expressed relative to a zero point on the sagittal plane through the user's head, and with a value increasing toward the right, as illustrated in FIG. 8A, $t_i$ is the normalized signal strength estimate obtained on the left side (left ear), and b and c are adjustable coefficients. In some examples, b and c are set to 5 and 0.17, respectively. In Eq. 1, the signal strength of the auricular muscle is assumed to be normalized, such that the normalized signal strength equals zero when the measured strength of muscle activity does not significantly exceed a threshold, which may correspond to the noise floor of the measurement device, and the normalized signal strength equals 1 when the measured strength of muscle activity is maximal. Eq. 1 is applicable when $t_l$ is greater than 0 and less than 1. If $t_l=1$, processing system 114 may estimate the angle of attention to be equal to 180 degrees, which corresponds to a sound source located in the back of the user's head. However, in practical applications, ti is less than 0.995, which corresponds approximately to 60 degrees. Due to the shape of the relationship between muscle-activity signal strength and the angle, the precision of the angle estimate may decrease as the normalized signal strength approaches 1. If $t_l=0$, processing system 114 may estimate the angle of attention to be smaller than 0 and, if the corresponding estimate of auricular muscle signal strength obtained on the right side of the user's head is available, processing system 114 may estimate the angle of attention more precisely based on the auricular muscle signal strength estimate obtained on the right side of the user's head, e.g., using the following equation:

$$a_r = -(-\ln(1/t_r - 1) + b)/c \quad \text{(Eq. 2)}$$

In Eq. 2, $\ln(\cdot)$ denotes the natural logarithm function and $a_r$ is the computed angle of attention (in degrees, expressed relative to a zero point on the sagittal plane through the user's head, with a value decreasing toward the left, as illustrated in FIG. 8A), $t_r$ is the normalized signal strength estimate obtained on the right side (right ear), and b and c are adjustable coefficients, as in Eq. 1. If $t_r=1$, processing system 114 may estimate $a_r$ to be equal to −180 degrees. If $t_r=1$, processing system 114 may estimate the angle of attention to be larger than 0, and processing system 114 may estimate this angle more precisely using Eq. 1, provided that a valid, corresponding estimate of signal strength obtained on the left side (left ear) of user 104 is available.

While the examples above illustrate the use of Eqs. 1 and 2 to compute deterministic estimates of attention angles, processing system 114 may use these equations, or similar or related ones, in the context of probabilistic mathematical models and computational methods. For example, processing system 114 may use maximum likelihood or Bayesian models or methods. For example, processing system 114 may use Bayesian computational methods, such as Markov-chain or hybrid Monte-Carlo methods, or approximate Bayesian inference methods, in conjunction with a generative probabilistic model based on inverse equations to Eqs. 1 and 2, to compute one or more angle of attention estimates, or posterior probabilistic distributions for these estimates, which may be used to quantify the precision of the estimates. Information about the precision of such estimates may subsequently be used by the processor to determine whether or not to send a particular control signal to a sound processing device (e.g., sound processor 606 (FIG. 6)). For example, if the precision is lower than a threshold, below which angle estimates are deemed too unreliable to warrant a particular change in a parameter of audio system 100 (e.g., a change in a parameter of a directional microphone mode), processing system 114 may not generate an electronic signal that triggers such a change in the parameters of audio system 100. For instance, processing system 114 may or may not change a processing mode of audio system 100.

In some examples where point estimates of both a left angle and a right angle are available, processing system 114 may combine these estimates (e.g., using a triangulation equation) to estimate a distance of a sound source that triggered an auditory reaction in user 104, or toward which the user's auditory attention is being directed, as illustrated schematically in FIG. 8A. Specifically, denoting as $\hat{a}_r(t)$ and $\hat{a}_l(t)$ estimates of the angles between (a) a line 800 passing through the user's current auditory attention locus and a reference point on the user's right ear (for $\hat{a}_r(t)$) or a line 802 passing through the user's current auditory locus and a reference point on the user's left ear (for $\hat{a}_l(t)$), and (b) a coronal plane 804 passing through the user's left and right ear canals, and denoting as $d_{lr}$ the distance between the reference points on the user's left and right ears, processing system 114 may compute the distance, denoted $d_r$, between the right ear reference point and the current locus of the user's auditory attention focus as:

$$d_r = d_{lr} \sin(\hat{a}_r(t)/180\pi)/\sin((\hat{a}_l(t) - \hat{a}_r(t))/180\pi). \quad \text{(Eq. 3)}$$

Similarly, processing system 114 may compute the distance, denoted di, between the left ear reference point and the current locus of the user's auditory attention focus as:

$$d_l = d_{lr} \sin(\hat{a}_l(t)/180\pi)/\sin((\hat{a}_l(t) - \hat{a}_r(t))/180\pi). \quad \text{(Eq. 4)}$$

When multiple angle or distance estimates, which may result from the use of additional sensors and signals, such as EOG signals or head-motion signals, are available, processing system 114 may implement a mathematical combination of these estimates, to yield a more accurate, more precise, or more robust estimate. For example, denoting as v a n-dimensional column vector (mathematical array) of angle estimates, $\hat{a}_1, \hat{a}_2, \ldots$, to $\hat{a}_n$, processing system 114 may combine these estimates to yield a further estimate, $\hat{a}_c$, as follows, $$\hat{a}c = w^T v, \quad \text{(Eq. 5)}$$

In Eq. 5, w is a n-dimensional column vector of suitably chosen weights (e.g., each weight being positively and monotonically related to the signal-to-noise ratio, or to the inverse precision, associated with the angle estimate corresponding to the weight), and the uppercase T denotes the vector transpose operator of linear algebra.

In some examples, processing system 114 comprises one or more sensors for measuring eye signals. The eye signals comprise at least one of eye-movement signals of user 104 or eye-position signals of user 104. For instance, the eye signals may comprise EOG signals, video signals of the eyes of user 104, or other signals indicative of movements of the eyes of user 104. In examples where the eye signals are EOG signals, the sensors for measurement the EOG signals may include electrodes. The electrodes for generating the EOG signals may be in the ear canal of user 104, or they may be placed elsewhere, for example, closer to at least one of the two eyes of user 104. Processors 102 may combine such eye signals with the periauricular muscle signals mathematically, in order to compute a combined signal. The combined signal may provide a better estimate of the angle corresponding to the direction of the user's current auditory attention locus. For example, if the user's eyes move in the direction corresponding to the user's auditory attention locus, processing system 114 may compute a weighted mean of the target-angle estimate (in complex-number form) computed based on the eye-movement signal, and of the target-angle estimate (in complex-number form) computed based on the periauricular muscle signals, as follows, $$\hat{\theta} = \arg(w_a e(i\theta_a) + (1-w_a)e(i\theta_e)) \quad \text{(Eq. 6)}$$

In Eq. 6, $\theta_a$ is the angle of the user's auditory attention locus computed using EMG signals, $\theta_e$ is the angle of the user's auditory attention locus computed using eye signals only, $w_a$ is the relative weight of the angle information derived from an analysis of the user's acoustic environment, and $\hat{\theta}$ is the resulting estimate of the user's auditory attention target, obtained by combining mathematically the periauricular-muscle and eye signals. In some examples, processing system 114 may decompose EMG signals into a component related to the deformation signals and a component unrelated to the deformation signals. In such examples, $\theta_a$ is the angle of the user's auditory attention locus computed using the components of the EMG signals unrelated to the deformation signals. If the relative weight, $w_a$, is chosen appropriately, a more accurate and precise estimate of the direction of the user's auditory attention can be obtained in this way, than might be possible based on the eye signals alone, or on the periauricular muscle signals alone. For example, the weight may be inversely related to the measurement error of the periauricular muscle signals, relative to the measurement error of the eye-movement signal.

In some examples, processing system 114 comprises electrodes for measuring brain signals of user 104. For instance, electrodes 108 (FIG. 1) may include electrodes for generating EEG signals of user 104 as well as electrodes for generating EMG signals indicative of activity of one or more intrinsic auricular muscles. The electrodes for generating the EEG signals may be in one or more ear canals of user 104. Furthermore, in this example, processing system 114 may generate a combined signal based on the brain signals and the EMG signals. Processing system 114 may use the combined signal to generate a more accurate and precise estimate of the angle corresponding to the direction in which the user's auditory attention is oriented, than might be achievable using either type of signal alone. For example, the mathematical combination of the EEG and EMG signals may take the same form as described in Eq. 6, with the angle estimate computed using eye signals replaced by an angle estimate computed using EEG signals. The latter estimate may be computed using existing techniques for processing EEG signals such as, for example, as described in Wong et al. "Decoding Speech Sound Source Direction from Electroencephalography Data," ARO MidWinter Meeting, February 2016 (2016). As described in Wong, subjects kept their eyes fixated straight ahead while a 64-channel EEG was recorded. A 3-level wavelet decomposition was then performed to split the data into 0-4, 4-8 Hz, 8-16 Hz and 16-32 Hz bands. For each band, the 4 independent components that had the largest power were taken. Over data segments of 5 seconds, the power within each component was then computed for each band. A deep neural network was trained on these features, using stochastic backpropagation. The output of the network was the angle of the incoming sound source.

In some examples, processing system 114 obtains head signals of user 104 from one or more sensors. The head signals of user 104 are indicative of head movements and/or head positions of user 104. In some examples, the sensors for generating the head signals comprises one or more of accelerometers, gyroscopes, or other types of sensors to determine the head signals. For instance, the sensors for generating the head signals may include IMU 426 (FIG. 4). Processing system 114 may generate, based on the head signals and the EMG signals, a combined signal that provides a more accurate and precise estimate of the direction toward the user's current auditory attention locus. For example, processing system 114 may determine the direction toward the user's current auditory attention locus by using an equation similar to Eq. 6, but using a direction computed based on the head signals and a direction computed using EMG signals.

Figure 8B:
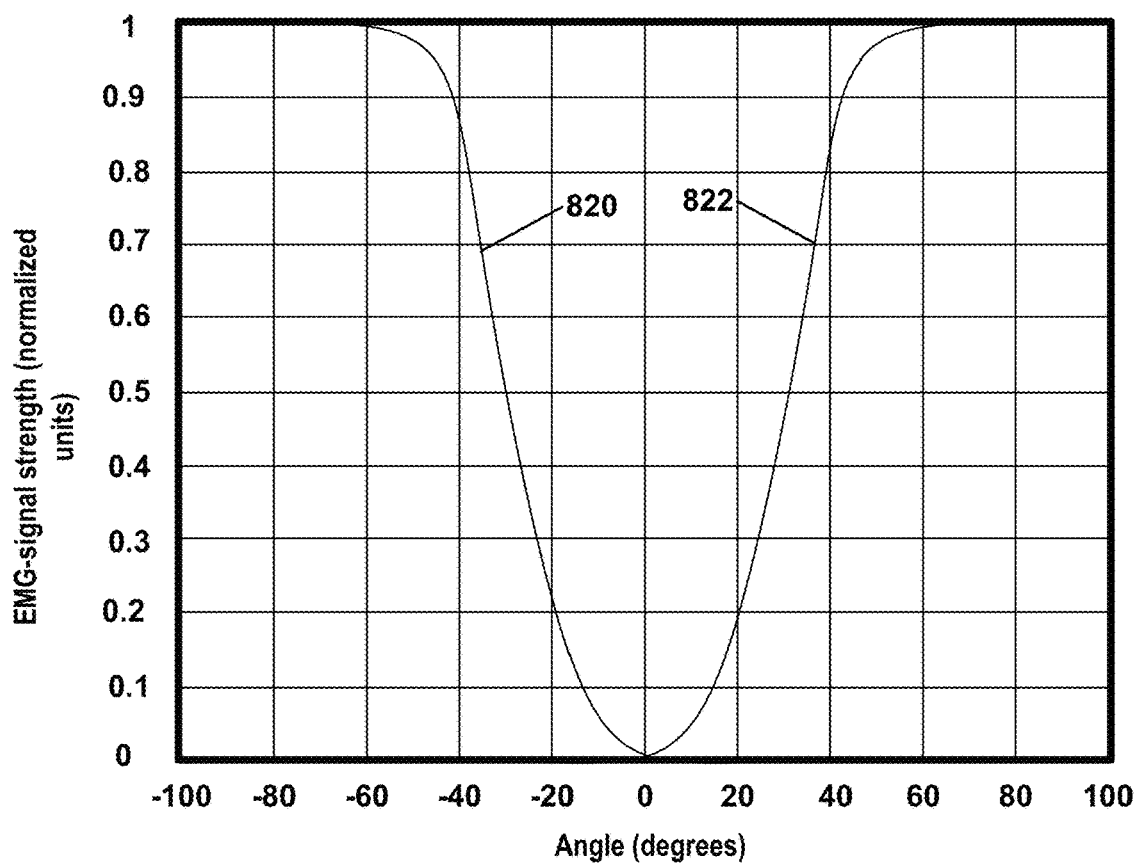
FIG. 8B is a conceptual diagram providing an example of how a processing system may combine angle estimates of a left and right side to estimate the distance of a sound source, which is the object of a user's attention, relative to the user.

FIG. 8B is a conceptual diagram providing an example of how processing system 114 may combine angle estimates of the left and right side to estimate the distance of a sound source, which is the object of the user's attention, relative to user 104. In the example of FIG. 8B, line 820 corresponds to a normalized activation level of a left transverse auricular muscle and line 822 corresponds to a normalized activation level of a right transverse auricular muscle. As shown in the example of FIG. 8B, maximum activation of the left transverse auricular muscle with minimum activation of the right transverse auricular muscle corresponds to a direction toward the user's auditory attention locus of approximately −75 to −100 degrees. Conversely, maximum activation of the right transverse auricular muscle with minimum activation of the left transverse auricular muscle corresponds to a direction toward the user's auditory attention locus of approximately 75 to 100 degrees.

Although this disclosure describes the examples of FIG. 8A and FIG. 8B primarily with respect to determining an azimuth angle based on EMG signals indicative of activation of the transverse auricular muscle, the examples of FIG. 8A and FIG. 8B may also apply with respect to determining an elevation angle based on EMG signals indicative of activation of the oblique auricular muscle.

In addition to, or instead of, Eqs. 1-6, processing system 114 may use statistical learning or machine-learned models, such as logistic regression and neural networks, to compute estimates of an attentional angle or distance, based on the measured concha EMG signals and the measured ear canal deformation signals. The use of such statistical learning or machine-learned models may comprise, as a first step, training a model to learn the association between some aspect of the measured biological signal, and a quantity of interest (e.g., an angle or distance). Alternatively, or in addition, the statistical- and machine-learned models may comprise unsupervised-learning algorithms, which utilize statistical regularities in input signals to compute features corresponding to mathematical transformations or combinations of these signals. Processing system 114 may then use the machine-learned model to generate information regarding the user's auditory attention state, such as a direction toward or distance to the user's current auditory attention locus. One potential advantage of this approach is that the designer of the system need not necessarily design a problem-specific algorithm, but instead may use a generic algorithm. Thus, in some examples, processing system 114 may apply a machine-learned model that generates the information regarding the auditory attention state of user 104 based on the deformation signal, the EMG signal, and/or other types of signals.

The use of machine-learned models may be particularly advantageous in applications where signals from other intrinsic auricular muscles than the transverse auricular muscle measured by an ear-worn device such as the one described in this application, need to be used instead of, or in addition to, transverse auricular muscle signals. For example, processing system 114 may use machine-learned models to learn statistical regularities in a relationship between, for example, EMG signals from an electrode positioned in the concha of a user to detect activity of an oblique auricular muscle, and auditory reactions of user 104, or an auditory attention of a user, or listening intentions of a user. In some examples, processing system 114 may continue to train the machine-learned models during a time that user 104 is using hearing instruments 102.

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations. Furthermore, with respect to examples that involve personal data regarding a user, it may be required that such personal data only be used with the permission of user 104.

The following is a non-limiting list of aspects in accordance with one or more techniques of this disclosure.

Aspect 1: A method for controlling a parameter of an audio system includes obtaining, by a processing system, a deformation signal generated by a deformation sensor, wherein the deformation signal is indicative of a deformation of an ear of a user of a hearing instrument; obtaining, by the processing system, an electromyographic (EMG) signal generated by an electrode in a concha of the user, wherein the EMG signal is indicative of activity of an intrinsic auricular muscle of the user; generating, by the processing system, information regarding an auditory attention state of the user based on the deformation signal and the EMG signal; and controlling, by the processing system, based on the information regarding the auditory attention state of the user, the parameter of the audio system.

Aspect 2: The method of aspect 1, wherein the deformation sensor is positioned on an anterior-inferior surface of an ear canal of the ear of the user.

Aspect 3: The method of any of aspects 1-2, wherein the electrode abuts a body of an antihelix of the user and the intrinsic auricular muscle is a transverse auricular muscle of the user.

Aspect 4: The method of any of aspects 1-2, wherein the intrinsic auricular muscle is an oblique auricular muscle of the user.

Aspect 5: The method of any of aspects 1-4, wherein generating the information regarding the auditory attention state of the user comprises: determining, by the processing system, based on the deformation signal, whether the deformation of the ear of the user was caused by a movement of a jaw of the user; and based on the deformation of the ear of the user not having been caused by the movement of the jaw of the user, generating, by the processing system, based on the EMG signal, the information regarding the auditory attention state of the user.

Aspect 6: The method of any of aspects 1-5, wherein generating the information regarding the auditory attention state comprises generating, by the processing system, based on the deformation signal and the EMG signal, information regarding a direction toward a current auditory attention locus of the user.

Aspect 7: The method of aspect 6, wherein the parameter corresponds to whether a direction processing mode is active, and controlling the parameter comprises activating, by the processing system, the directional processing mode based on the direction toward the current auditory attention locus of the user.

Aspect 8: The method of any of aspects 6-7, wherein: generating the information regarding the auditory attention state of the user further comprises generating, by the processing system, information indicating a distance to the current auditory attention locus of the user, and controlling the parameter of the audio system comprises controlling, by the processing system, the parameter of the audio system based on the direction toward the current auditory attention locus of the user and the distance to the current auditory attention locus of the user.

Aspect 9: The method of any of aspects 1-8, wherein: the method further comprises obtaining, by the processing system, an additional signal generated by an additional sensor, wherein the additional signal is an electroencephalogram (EEG) signal or an electrooculogram (EOG) signal, and generating the information regarding the auditory attention state of the user comprises generating, by the processing system, the information regarding the auditory attention state of the user based on the EMG signal, the deformation signal, and the additional signal.

Aspect 10: The method of any of aspects 1-9, wherein: the method further comprises obtaining, by the processing system, a head signal from an additional sensor, wherein the head signal is indicative of head movements of the user, wherein the additional sensor is an inertial measurement unit (IMU), and generating the information regarding the auditory attention state of the user comprises generating, by the processing system, the information regarding the auditory attention state of the user based on the EMG signal, the deformation signal, and the head signal.

Aspect 11: The method of any of aspects 1-10, wherein: generating the information regarding the auditory attention state of the user comprises applying, by the processing system, a machine-learned model that generates the information regarding the auditory attention state of the user based on the deformation signal and the EMG signal.

Aspect 12: The method of any of aspects 1-11, wherein: the electrode is a first electrode, the EMG signal is a first EMG signal, and the first electrode is positioned to detect activity of a transverse auricular muscle of the user, the method further comprises obtaining, by the processing system, a second EMG signal from a second electrode in the concha of the user, wherein the second electrode is positioned to detect activity of an oblique auricular muscle of the user, and generating the information regarding the auditory attention state of the user comprises generating, by the processing system, the information regarding the auditory attention state of the user based on the deformation signal, the first EMG signal, and the second EMG signal.

Aspect 13: An audio system includes a deformation sensor configured to generate a deformation signal indicative of a deformation of an ear of a user of a hearing instrument; an electrode configured to generate an electromyographic (EMG) signal indicative of activity of an intrinsic auricular muscle of the user of the hearing instrument; a processing system comprising one or more processing circuits, the processing system configured to: obtain the deformation signal generated by the deformation sensor; obtain the EMG signal generated by the electrode; generate information regarding an auditory attention state of the user based on the deformation signal and the EMG signal; and control, based on the information regarding the auditory attention state of the user, the parameter of the audio system.

Aspect 14: The audio system of aspect 13, wherein the audio system comprises an in-canal element configured to position the deformation sensor on an anterior-inferior surface of an ear canal of the ear of the user.

Aspect 15: The audio system of any of aspects 13-14, wherein the audio system comprises an intra-concha element configured to position the electrode so that the electrode abuts a body of an antihelix of the user and the intrinsic auricular muscle is a transverse auricular muscle of the user.

Aspect 16: The audio system of any of aspects 13-15, wherein the intrinsic auricular muscle is an oblique auricular muscle of the user.

Aspect 17: The audio system of any of aspects 13-16, wherein the processing system is configured to, as part generating the information regarding the auditory attention state of the user, the processing system: determine, based on the deformation signal, whether the deformation of the ear of the user was caused by a movement of a jaw of the user; based on the deformation of the ear of the user not having been caused by the movement of the jaw of the user, generate, based on the EMG signal, the information regarding the auditory attention state of the user; and based on the deformation of the ear of the user having been caused by the movement of the jaw of the user, refrain from generating the information regarding the auditory attention state of the user based on the EMG signal.

Aspect 18: The audio system of any of aspects 13-17, wherein the processing system is configured such that, as part of generating the information regarding the auditory attention state, the processing system generates, based on the deformation signal and the EMG signal, information regarding a direction toward a current auditory attention locus of the user.

Aspect 19: The audio system of aspect 18, wherein the processing system is configured such that, as part of controlling the parameter, the processing system activates a directional processing mode based on the direction toward the current auditory attention locus of the user.

Aspect 20: The audio system of any of aspects 18-19, wherein: the processing system is configured such that, as part of generating the information regarding the auditory attention state of the user, the processing system generates information indicating a distance to the current auditory attention locus of the user, and the processing system is configured such that, as part of controlling the parameter of the audio system, the processing system controls the parameter of the audio system based on the direction toward the current auditory attention locus of the user and the distance to the current auditory attention locus of the user.

Aspect 21: The audio system of any of aspects 13-20, wherein: the processing system is further configured to obtain an additional signal generated by an additional sensor, wherein the additional signal is an electroencephalogram (EEG) signal or an electrooculogram (EOG) signal, and the processing system is configured such that, as part of generating the information regarding the auditory attention state of the user, the processing system generates the information regarding the auditory attention state of the user based on the EMG signal, the deformation signal, and the additional signal.

Aspect 22: The audio system of any of aspects 13-21, wherein: the processing system is further configured to obtain a head signal from an additional sensor, wherein the head signal is indicative of head movements of the user, wherein the additional sensor is an inertial measurement unit (IMU), and the processing system is configured to generate the information regarding the auditory attention state of the user based on the EMG signal, the deformation signal, and the head signal.

Aspect 23: The audio system of any of aspects 13-22, wherein: the processing system is configured such that, as part of generating the information regarding the auditory attention state of the user, the processing system applies a machine-learned model that generates the information regarding the auditory attention state of the user based on the deformation signal and the EMG signal.

Aspect 24: The audio system of any of aspects 13-23, wherein: the electrode is a first electrode, the EMG signal is a first EMG signal, and the first electrode is positioned to detect activity of a transverse auricular muscle of the user, the audio system comprises a second electrode configured to generate a second EMG signal indicative of an activity of an oblique auricular muscle of the user, and the processing system is configured such that, as part of generating the information regarding the auditory attention state of the user, the processing system generates the information regarding the auditory attention state of the user based on the deformation signal, the first EMG signal, and the second EMG signal.

Aspect 25: A computer-readable storage medium having instructions stored thereon that, when executed, cause a processing system of an audio system to perform the methods of any of aspects 1-12.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method for controlling a parameter of an audio system, the method comprising:
    obtaining, by a processing system, a deformation signal generated by a deformation sensor, wherein the deformation signal is indicative of a deformation of an ear of a user of a hearing instrument;
    obtaining, by the processing system, an electromyographic (EMG) signal generated by an electrode in a concha of the user, wherein the EMG signal is indicative of activity of an intrinsic auricular muscle of the user;
    determining, by the processing system, based on the deformation signal, whether the deformation of the ear of the user was caused by a movement of a jaw of the user;
    based on the deformation of the ear of the user not having been caused by the movement of the jaw of the user, generating, by the processing system, based on the EMG signal, information regarding an auditory attention state of the user; and controlling, by the processing system, based on the information regarding the auditory attention state of the user, the parameter of the audio system.

2. The method of claim 1, wherein:

the deformation sensor is positioned on an anterior-inferior surface of an ear canal of the ear of the user, and the electrode abuts a body of an antihelix of the user and the intrinsic auricular muscle is a transverse auricular muscle of the user.

3. The method of claim 1, wherein generating the information regarding the auditory attention state comprises generating, by the processing system, based on the the EMG signal, information regarding a direction toward a current auditory attention locus of the user.

4. The method of claim 3, wherein:

generating the information regarding the auditory attention state of the user further comprises generating, by the processing system, information indicating a distance to the current auditory attention locus of the user, and controlling the parameter of the audio system comprises controlling, by the processing system, the parameter of the audio system based on the direction toward the current auditory attention locus of the user and the distance to the current auditory attention locus of the user.

5. The method of claim 1, wherein:

the method further comprises obtaining, by the processing system, an additional signal generated by an additional sensor, wherein the additional signal is an electroencephalogram (EEG) signal or an electrooculogram (EOG) signal, and generating the information regarding the auditory attention state of the user comprises generating, by the processing system, the information regarding the auditory attention state of the user based on the EMG signal and the additional signal.

6. The method of claim 1, wherein:

the method further comprises obtaining, by the processing system, a head signal from an additional sensor, wherein the head signal is indicative of head movements of the user, wherein the additional sensor is an inertial measurement unit (IMU), and generating the information regarding the auditory attention state of the user comprises generating, by the processing system, the information regarding the auditory attention state of the user based on the EMG signal and the head signal.

7. The method of claim 1, wherein:

the electrode is a first electrode, the EMG signal is a first EMG signal, and the first electrode is positioned to detect activity of a transverse auricular muscle of the user, the method further comprises obtaining, by the processing system, a second EMG signal from a second electrode in the concha of the user, wherein the second electrode is positioned to detect activity of an oblique auricular muscle of the user, and generating the information regarding the auditory attention state of the user comprises generating, by the processing system, the information regarding the auditory attention state of the user based on the first EMG signal and the second EMG signal.

8. An audio system comprising:

a deformation sensor configured to generate a deformation signal indicative of a deformation of an ear of a user of a hearing instrument;

an electrode configured to generate an electromyographic (EMG) signal indicative of activity of an intrinsic auricular muscle of the user of the hearing instrument;

a processing system comprising one or more processing circuits, the processing system configured to:

obtain the deformation signal generated by the deformation sensor;

obtain the EMG signal generated by the electrode;

determine, based on the deformation signal, whether the deformation of the ear of the user was caused by a movement of a jaw of the user;

based on the deformation of the ear of the user not having been caused by the movement of the jaw of the user, generate information regarding an auditory attention state of the user based on the EMG signal; and control, based on the information regarding the auditory attention state of the user, a parameter of the audio system.

9. The audio system of claim 8, wherein the audio system comprises an in-canal element configured to position the deformation sensor on an anterior-inferior surface of an ear canal of the ear of the user.

10. The audio system of claim 8, wherein the audio system comprises an intra-concha element configured to position the electrode so that the electrode abuts a body of an antihelix of the user and the intrinsic auricular muscle is a transverse auricular muscle of the user.

11. The audio system of claim 8, wherein the intrinsic auricular muscle is an oblique auricular muscle of the user.

12. The audio system of claim 8, wherein the processing system is configured to, as part generating the information regarding the auditory attention state of the user, the processing system:

based on the deformation of the ear of the user having been caused by the movement of the jaw of the user, refrains from generating the information regarding the auditory attention state of the user based on the EMG signal.

13. The audio system of claim 8, wherein the processing system is configured such that, as part of generating the information regarding the auditory attention state, the processing system generates, based on the EMG signal, information regarding a direction toward a current auditory attention locus of the user.

14. The audio system of claim 13, wherein the processing system is configured such that, as part of controlling the parameter, the processing system activates a directional processing mode based on the direction toward the current auditory attention locus of the user.

15. The audio system of claim 13, wherein:

the processing system is configured such that, as part of generating the information regarding the auditory attention state of the user, the processing system generates information indicating a distance to the current auditory attention locus of the user, and the processing system is configured such that, as part of controlling the parameter of the audio system, the processing system controls the parameter of the audio system based on the direction toward the current auditory attention locus of the user and the distance to the current auditory attention locus of the user.

16. The audio system of claim 8, wherein:
the processing system is further configured to obtain an additional signal generated by an additional sensor, wherein the additional signal is an electroencephalogram (EEG) signal or an electrooculogram (EOG) signal, and
the processing system is configured such that, as part of generating the information regarding the auditory attention state of the user, the processing system generates the information regarding the auditory attention state of the user based on the EMG signal and the additional signal.

17. The audio system of claim 8, wherein:
the processing system is further configured to obtain a head signal from an additional sensor, wherein the head signal is indicative of head movements of the user, wherein the additional sensor is an inertial measurement unit (IMU), and
the processing system is configured to generate the information regarding the auditory attention state of the user based on the EMG signal and the head signal.

18. The audio system of claim 8, wherein:
the processing system is configured such that, as part of generating the information regarding the auditory attention state of the user, the processing system applies a machine-learned model that generates the information regarding the auditory attention state of the user based on the EMG signal.

19. The audio system of claim 8, wherein:
the electrode is a first electrode, the EMG signal is a first EMG signal, and the first electrode is positioned to detect activity of a transverse auricular muscle of the user,
the audio system comprises a second electrode configured to generate a second EMG signal indicative of an activity of an oblique auricular muscle of the user, and
the processing system is configured such that, as part of generating the information regarding the auditory attention state of the user, the processing system generates the information regarding the auditory attention state of the user based on the first EMG signal and the second EMG signal.

20. One or more non-transitory computer-readable storage media having instructions stored thereon that, when executed by a processing system of an audio system, cause the processing system to:
obtain a deformation signal generated by a deformation sensor, wherein the deformation signal is indicative of a deformation of an ear of a user of a hearing instrument;
obtain an electromyographic (EMG) signal generated by an electrode in a concha of the user, wherein the EMG signal is indicative of activity of an intrinsic auricular muscle of the user;
determine, based on the deformation signal, whether the deformation of the ear of the user was caused by a movement of a jaw of the user;
based on the deformation of the ear of the user not having been caused by the movement of the jaw of the user, generate information regarding an auditory attention state of the user based on the EMG signal; and
control, based on the information regarding the auditory attention state of the user, a parameter of the audio system.

* * * * *